United States Patent [19]

Markley et al.

[11] 4,371,537

[45] Feb. 1, 1983

[54] SULFUR-SUBSTITUTED PHENOXYPYRIDINES HAVING ANTIVIRAL ACTIVITY

[75] Inventors: Lowell D. Markley, Midland, Mich.; Yulan C. Tong, Walnut Creek, Calif.; Steven G. Wood, Orem, Utah

[73] Assignee: The Dow Chemical Company, Midland, Mich.

[21] Appl. No.: 292,467

[22] Filed: Aug. 13, 1981

[51] Int. Cl.³ .................. A61K 31/44; C07D 212/63
[52] U.S. Cl. ................... 424/263; 546/270; 546/294; 546/296
[58] Field of Search .......... 546/296, 270, 294; 424/263

[56] References Cited

U.S. PATENT DOCUMENTS

| | | | |
|---|---|---|---|
| 3,429,689 | 2/1969 | Duerr et al. | 546/295 |
| 3,535,328 | 10/1970 | Zielinski | 546/275 |
| 3,549,647 | 12/1970 | Johnston | 546/296 |
| 3,639,413 | 2/1972 | Domenico | 546/295 |
| 3,654,291 | 4/1972 | Witzel et al. | 546/306 |
| 3,655,897 | 4/1972 | Witzel | 546/306 |
| 3,687,959 | 8/1972 | Zielinski | 546/291 |
| 3,719,682 | 3/1973 | Domenico | 546/295 |
| 3,732,234 | 5/1973 | Domenico | 546/295 |
| 3,931,201 | 1/1976 | Johnston | 71/94 |
| 3,954,782 | 5/1976 | Fieckenstein et al. | 546/306 |
| 3,956,294 | 5/1976 | Fieckenstein et al. | 546/306 |
| 3,962,265 | 6/1976 | Johnston | 71/94 |
| 3,980,659 | 9/1976 | Fieckenstein et al. | 546/306 |
| 4,003,733 | 1/1977 | Johnston | 71/94 |
| 4,055,650 | 10/1977 | Delaoge et al. | 546/295 |
| 4,067,983 | 1/1978 | Poschel et al. | 424/263 |
| 4,080,443 | 3/1978 | Malhotra | 546/306 |
| 4,132,784 | 1/1979 | Malhotra | 546/306 |
| 4,212,980 | 7/1980 | Butler | 546/288 |
| 4,229,457 | 10/1980 | Butler | 424/263 |

*Primary Examiner*—Jane T. Fan

[57] ABSTRACT

Sulfur-substituted phenoxypyridines having antiviral activity are disclosed. Methods of using the sulfur-substituted phenoxypyridines to employ their antiviral activity are also disclosed as well as pharmaceutically-acceptable compositions thereof.

67 Claims, No Drawings

SULFUR-SUBSTITUTED PHENOXYPYRIDINES HAVING ANTIVIRAL ACTIVITY

SUMMARY OF THE INVENTION

The present invention is directed to an antiviral compound corresponding to the formula:

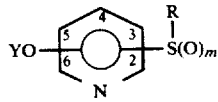
(I)

wherein m represents the integer 0, 1 or 2; R represents an alkyl group of from 1 to 7 carbon atoms, inclusive, such as methyl, ethyl, propyl, isopropyl, t-butyl, n-hexyl and n-heptyl, a cycloalkyl group of 5 or 6 carbon atoms, such as cyclopentyl and cyclohexyl, or a Ar-$(CH_2)_q$-group wherein q represents the integer 0, 1, 2 or 3 and Ar represents an aryl group of from 6 to 10 carbon atoms, inclusive, which aryl group is optionally substituted with 1 to 3 substituents each independently selected from bromo, chloro, fluoro, methyl or methoxy; Y represents the radical

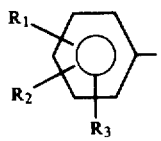

wherein $R_1$ and $R_2$ each independently represent hydrogen, bromo, chloro, fluoro, iodo, cyano, nitro, acetyl or the following moieties:

(a) a benzyl, phenoxy or benzoyl group, wherein the benzene ring of the benzyl, phenoxy or benzoyl group is optionally substituted with 1 to 3 substituents each independently selected from bromo, chloro, fluoro, methyl or methoxy such as 4-chlorophenoxy, 4-bromophenoxy, 4-fluorophenoxy, 4-methylphenoxy, 4-methoxyphenoxy, 3-chlorophenoxy, 2-chlorophenoxy, 2,3-dichlorophenoxy, 2,4-dichlorophenoxy, 3,4-dichlorophenoxy, 3,4,5-trichlorophenoxy, 3-bromo-4-chlorophenoxy, 4-methyl-2-chlorophenoxy, 2-methyl-4-chlorophenoxy, 2,4-dimethylphenoxy, 4-methyl-2,6-dichlorophenoxy, 2-bromo-4-methyl-6-chlorophenoxy and similarly substituted benzyl and benzoyl moieties;

(b) an alkyl group of 1 to 4 carbon atoms, inclusive, optionally substituted with 1 to 4 substituents each independently selected from bromo, chloro or fluoro such as methyl, ethyl, propyl, isopropyl, t-butyl, sec-butyl, n-butyl, isobutyl, trifluoromethyl and 2,2-dichloro-1,1-difluoroethyl;

(c) $R_4X$-, wherein X represents an oxygen or sulfur atom; and $R_4$ represents an alkyl group of from 1 to 3 carbon atoms, inclusive, the alkyl portion optionally substituted with 1 to 4 substituents each independently selected from bromo, chloro or fluoro such as methylthio, ethylthio, propylthio, isopropylthio, methoxy, ethoxy, propoxy, isopropoxy, trifluoromethoxy, trifluoromethylthio (-$SCF_3$), 2,2-dichloro-1,1-difluoroethoxy, and 2-chloro-1,1,2-trifluoroethoxy; or (d) alternatively $R_1$ and $R_2$ taken together represent methylenedioxy; and $R_3$ represents hydrogen, bromo, chloro, fluoro or iodo; provided that:

(1) in those situations where the —OY radical is attached to the pyridine ring at the 3 position then the

radical is attached at the 5 position;

(2) in those situations where the —OY radical is attached to the pyridine ring at the 4 position then the

radical is attached at the 2 position;

(3) in those situations where m represents the integer 0 or 1; then
  (i) the radical —OY must be attached to the pyridine ring at the 2 position and the

radical at either the 3 or 5 positions; or
  (ii) the radical —OY must be attached to the pyridine ring at the 3 position and the

radical at the 5 position; and (4) in those situations where R is Ar-$(CH_2)_q$- or optionally substituted Ar-$(CH_2)_q$- and $R_2$ and $R_3$ are both hydrogen, then $R_1$ is a substituent other than hydrogen.

Representative Ar-$(CH_2)_q$- groups and substituted -Ar-$(CH_2)_q$- groups are, for example, phenyl, 4-chlorophenyl, 4-bromophenyl, 4-fluorophenyl, 4-methylphenyl, 4-methoxyphenyl, 3-chlorophenyl, 2-chlorophenyl, 2,3-dichlorophenyl, 2,4-dichlorophenyl, 3,4-dichlorophenyl, 3-bromo-4-chlorophenyl, 4-methyl-2-chlorophenyl, 2-methyl-4-chlorophenyl, 2,4-dimethylphenyl, 2,4,6-trichlorophenyl, 3,4,5-trichlorophenyl, 4-methyl-2,6-dichlorophenyl, 2-bromo-4-methyl-6-chlorophenyl, naphthyl, 6-chloronaphthyl, 6-methylnaphthyl, 6,7-dichloronaphthyl, 6,7-dimethylnaphthyl, benzyl, 4-chlorobenzyl, 4-bromobenzyl, 4-fluorobenzyl, 4-methylbenzyl, 4-methoxybenzyl, 3-chlorobenzyl, 2-chlorobenzyl, 2,4-dichlorobenzyl, 3,4-dichlorobenzyl, 4-methyl-2-chlorobenzyl, 2-methyl-4-chlorobenzyl, 2,4-dimethylbenzyl, 2,4,6-trichlorobenzyl, 3,4,5-trichlorobenzyl, 4-methyl-2,6-dichlorobenzyl, and similar unsubstituted and substituted phenylethyl, phenylpropyl, phenylisopropyl, naphthylmethyl, naphthylethyl, naphthylpropyl and naphthylisopropyl moieties.

Preferred compounds for antiviral use are those compounds of formula I in which m represents the integer 0, 1 or 2; R represents an alkyl group of from 1 to 7 carbon atoms, inclusive; and with regard to Y, $R_1$ and $R_2$ each independently represent hydrogen, bromo, chloro, fluoro, benzoyl, trifluoromethylthio, methylthio or cyano; and $R_3$ represents hydrogen, bromo, chloro or fluoro.

Of the preferred compounds, those compounds in which m represents the integer 0, 1 or 2; R represents methyl or ethyl; and with regard to Y, $R_1$ represents benzoyl, bromo or chloro; and $R_2$ and $R_3$ each independently represent hydrogen, bromo or chloro are especially preferred.

Compounds in which m represents the integer 2; R represents methyl or ethyl; and with regard to Y, $R_1$ represents bromo or chloro; $R_2$ represents hydrogen, bromo or chloro; and $R_3$ represents hydrogen are particularly preferred.

Of the compounds of formula I, those compounds in which the radical —OY is attached to the pyridine ring at the 2 position and the

radical is attached to the pyridine ring at the 5 position are the preferred isomers. Thus the most preferred compounds of the invention are the 5-(R-thio and/or R-sulfinyl and/or R-sulfonyl)-2-phenoxypyridine compounds having the preferred meanings for m, R and Y set forth previously herein.

The compounds disclosed herein, that is, the antiviral compounds of formula I, can be used to inhibit viral replication by contacting a virus and preferably, virus host cells with an effective amount of the appropriate subject compound. The present invention is further directed to methods of using the compounds of the invention as antiviral agents in which a virus or virus host cell (i.e., a cell susceptible to infection by the virus) is contacted with an effective amount of one or more of the subject compounds. The present invention is also directed to antiviral compositions which can contain from about 0.00001 percent (%) or less to about 99% by weight of the active compound in combination with a pharmaceutically-acceptable carrier. Typically, in those combinations employing a low percentage of active compound, the pharmaceutically-acceptable carrier is in liquid form, therefore a composition containing 0.00001% or less by weight of active compound is equivalent to a composition containing about 0.1 microgram (μg) or less of the active compound per milliliter (ml) of carrier.

DETAILED DESCRIPTION OF THE INVENTION

The (R-thio)-substituted-phenoxypyridines, (described by formula I when m represents the integer 0 and R and Y are as defined for formula I) can be prepared by at least one of the following methods:

METHOD I

The 5-(R-thio)-2-phenoxypyridines and 3-(R-thio)-2-phenoxypyridines are prepared as follows:

A nitro-substituted-phenoxypyridine of the formula:

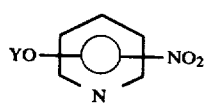
(II)

(wherein the —NO$_2$ moiety is attached to the pyridine ring at the 3 or 5 position and the radical —OY is attached at the 2 position) is formed by reacting a 5-nitro-2-halopyridine or 3-nitro-2-halopyridine with an appropriate substituted-phenol represented by the formula:

Y—OH     (III)

wherein Y is as defined for formula I with regard to both the formula II and formula III compounds.

The choice of the nitro-substituted-halopyridine dictates which (R-thio)-substituted-phenoxypyridine is obtained. In the nitro-substituted-halopyridine, halo represents bromo, chloro, fluoro or iodo; however chloro is preferred. The nitro-substituted-halopyridine starting materials are available commercially, known in the art or readily prepared by known procedures, see Great Britain Pat. No. 1,038,530.

The reaction of the nitro-substituted-halopyridine and the substituted-phenol is accomplished by contacting and mixing the reactants in a suitable inert organic solvent such as dimethyl sulfoxide (DMSO), tetrahydrofuran (THF) and dimethylformamide (DMF) in the presence of a base at a temperature of from about 20° C. to about 120° C. for a time sufficient to obtain the desired nitro-substituted-phenoxypyridine.

Following reaction, the nitro-substituted-phenoxypyridine is recovered from the reaction mixture employing traditional techniques well known in the art, such as dilution with water and filtration. Purification is accomplished by conventional techniques such as recrystallization.

The nitro-substituted-phenoxypyridine is then reduced to the corresponding amino-substituted-phenoxypyridine represented by the formula:

(IV)

wherein Y is as defined for formula I; and the —NH$_2$ moiety is attached to the pyridine ring at the 3 or 5 position and the radical —OY is attached at the 2 position; utilizing well known procedures, for example, hydrogenation in the presence of a suitable noble metal catalyst such as palladium or by standard chemical means. The amino-substituted-phenoxypyridine is conveniently recovered and purified employing conventional procedures such as those described herein.

The amino-substituted-phenoxypyridine is then converted to the corresponding diazonium salt using well known procedures. For example, the diazonium salt is conveniently prepared by contacting and mixing the amino-substituted-phenoxypyridine with a mineral acid in a suitable solvent, such as a loweralkanol (e.g., methanol or ethanol), with the temperature kept below about 5° C. An aqueous solution of sodium nitrite is then added at a slow enough rate to maintain the reduced temperature. Immediately after preparation, the diazonium salt is recovered by conventional procedures, and then it is contacted and mixed with a solution of an alkali metal mercaptide of the formula CSR wherein C represents an alkali metal cation such as Na+ or K+; and R is as defined for formula I, for a time sufficient to obtain the desired (R-thio)-substituted-phenoxypyridine.

The alkali metal mercaptide solutions referred to above are prepared by placing the appropriate thiol (of the formula RSH wherein R is defined as for formula I) in a suitable solvent such as acetonitrile in the presence of a sufficient quantity of alkali metal hydroxide to ensure formation of the mercaptide ion.

METHOD II

Alternately, the 5-(R-thio)-2-phenoxypyridines and 3-(R-thio)-2-phenoxypyridines are prepared from the amino-substituted-phenoxypyridine compounds (represented by formula IV herein) as follows:

The amino-substituted-phenoxypyridine compound is converted to its diazonium salt utilizing well known procedures such as those described herein, and the diazonium salt is then reacted with potassium ethyl xanthate by contacting and mixing the diazonium salt with a solution of potassium ethyl xanthate in water under conditions sufficient to form the corresponding ethyl dithiocarbonate substituted compound of the formula:

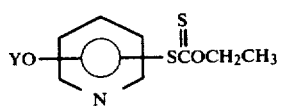

(V)

wherein Y is defined as for formula I; and the:

moiety is attached to the pyridine ring with respect to the radical —OY in the same manner as the —NH$_2$ moiety is attached as defined for formula IV.

The ethyl dithiocarbonate substituted compound is converted to the corresponding thiol, represented by the formula:

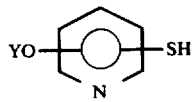

(VI)

(wherein Y is as defined for formula I; and the —SH moiety is attached to the pyridine ring with respect to the radical —OY in the same manner as the —NH$_2$ moiety is attached as defined for formula IV) by treating the ethyl dithiocarbonate compound with a suitable base such as ethylamine or an alkali metal hydroxide under conditions sufficient to form the corresponding salt. The salt is then treated with a mineral acid such as HCl to neutralize the base.

The thiol (i.e., formula VI compound) is then reacted with a suitable halo-substituted compound of the formula RL wherein R is defined as for formula I; and L represents bromo, chloro or iodo, by contacting and mixing the reactants in a suitable solvent such as acetonitrile and loweralkanols in the presence of a base for a time sufficient to obtain the desired (R-thio)substituted-phenoxypyridine compound.

METHOD III

The 5-(R-thio)-3-phenoxypyridines are prepared by reacting 2-cyano-3,5-dichloropyridine with the approriate thiol (of the formula RSH wherein R is defined as for formula I) in an inert organic solvent under conditions sufficient to form the R-thio substituted compounds (generally a mixture of 2-cyano-3-chloro-5-(R-thio)pyridine and 2-cyano-5-chloro-3-(R-thio)pyridine).

The R-thio substituted compounds are reacted with the appropriate substituted-phenol (represented by formula III) in a suitable inert organic solvent such as THF and DMSO in the presence of a base such as potassium t-butoxide (t-BuOK) and the resulting mixture refluxed for a time sufficient to obtain the substituted-phenoxy derivatives (i.e., generally a mixture of 2-cyano-3-(substituted-phenoxy)-5-(R-thio)pyridine and 2-cyano-5-(substituted-phenoxy)-3-(R-thio)pyridine).

The cyano moiety of the above-noted substituted-phenoxy derivatives can be hydrolyzed employing procedures well known in the art to give the pyridine-2-carboxylic acid derivatives (generally a mixture of 3-(substituted-phenoxy)-5-(R-thio)-pyridine-2-carboxylic acid and 5-(substituted-phenoxy)-3-(R-thio)-pyridine-2-carboxylic acid).

Decarboxylation of the pyridine-2-carboxylic acid derivatives employing standard procedures provides the desired 5-(R-thio)-3-phenoxypyridine compounds. Because the decarboxylation produces a single product it is unnecessary to separate the isomeric intermediates prepared in the various steps set forth herein.

The 5-(R-thio)-3-phenoxypyridines are separated from the reaction mixture and purified employing conventional procedures.

The 2-cyano-3,5-dichloropyridine starting material is readily prepared from 3,5-dichloropyridine-2-carboxylic acid (Beilstein, XXII, page 37) employing well known procedures.

The choice of the method utilized for the preparation of the (R-thio)-substituted-phenoxypyridine compounds will depend upon considerations such as the solubility and reactivity of the starting materials and intermediates and the nature of the desired final product.

METHOD IV

The (R-sulfinyl)-substituted-phenoxypyridines, (i.e., the 5-(R-sulfinyl)-2-phenoxypyridines, the 3-(R-sulfinyl)-2-phenoxypyridines and the 5-(R-sulfinyl)-3-phenoxypyridines described by formula I when m represents the integer 1 and R and Y are as defined for formula I), are conveniently prepared by oxidizing the appropriate (R-thio)-substituted-phenoxypyridine compound. Considerations such as the solubility and reactivity of the starting compound can dictate the choice of the most appropriate oxidizing agent and conditions to be employed for the oxidation. Such oxidation procedures are well known in the art, and are routinely accomplished employing oxidizing agents such as glacial acetic acid/hydrogen peroxide, trifluoroacetic acid/hydrogen peroxide, m-chloroperbenzoic acid, sodium metaperiodate, DABCO dibromide, and the like.

Certain of the (R-sulfonyl)-substituted-phenoxypyridines (i.e., the 5-(R-sulfonyl)-2-phenoxypyridines, the 3-(R-sulfonyl)-2-phenoxypyridines, and the 5-(R-sulfonyl)-3-phenoxypyridines) can also be prepared by oxidizing the appropriate (R-thio)-substituted-phenoxypyridine compound. In the preparation of the above-noted (R-sulfonyl)-substituted-phenoxypyridines well known oxidation procedures can be used, such as those described herein.

By varying the oxidizing agent, the concentration and amount of the oxidizing agent and the temperature, the oxidation reactions described herein can be modified so that a predominance of either the R-sulfonyl or R-sulfonyl moiety is obtained.

METHOD V

Certain of the (R-sulfonyl)-substituted-phenoxypyridine compounds described herein can be prepared utilizing bis(R-sulfonyl)pyridine intermediates as follows:

Those compounds of formula I which are 3-(R-sulfonyl)-2-phenoxypyridines or 5-(R-sulfonyl)-2-phenoxypyridines can also be prepared via intermediates of the formula:

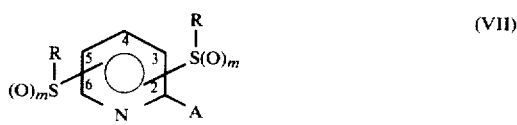

wherein the

moieties are attached to the pyridine ring either at the 3 and 6 positions or 5 and 6 positions; m represents the integer 0 or 2; R is as defined for formula I; and A represents hydrogen or a carboxyl group (—COOH), with the proviso that A is hydrogen when m is 2.

In the process of preparing the 3-(R-sulfonyl)-2-phenoxypyridine or 5-(R-sulfonyl)-2-phenoxypyridine derivatives, a 3,6-dihalo-pyridine-2-carboxylic acid or a 5,6-dihalo-pyridine-2-carboxylic acid (or their methyl esters) represented by the formula:

wherein $Z_1$ and $Z_2$ are attached to the pyridine ring at either the 3 and 6 positions or 5 and 6 positions; $Z_1$ and $Z_2$ each independently represent chloro, bromo, fluoro or iodo; and $R_5$ is hydrogen or methyl; is reacted with the appropriate mercaptan of the formula R-SH, wherein R is defined as for formula I. In the reaction of the dihalo-pyridine-2-carboxylic acid and the mercaptan a dichloro-pyridine-2-carboxylic acid or its methyl ester is preferred.

U.S. Pat. No. 3,317,549 describes 3,6-dichloropyridine-2-carboxylic acid and related esters. The compound 5,6-dichloropyridine-2-carboxylic acid is readily prepared from 2,3-dichloro-6-(trichloromethyl)pyridine (see U.S. Pat. No. 4,256,894) by hydrolysis employing the procedure described in U.S. Pat. No. 3,317,549.

When $R_5$ is methyl, the above reaction is conveniently accomplished by contacting and mixing the dihalo-pyridine-2-carboxylic acid methyl ester with the mercaptan in a suitable organic solvent, such as dimethylformamide (DMF) or dimethyl sulfoxide, in the presence of a base such as potassium t-butoxide (t-BuOK), sodium hydroxide or potassium hydroxide, at from about 100° C. to reflux temperature for a time sufficient to obtain the desired 3,6-bis(R-thio)pyridine-2-carboxylic acid salt or 5,6-bis(R-thio)pyridine-2-carboxylic acid salt. Usually, a reaction time of about 1 to 10 hours is sufficient for the above reaction.

When $R_5$ is hydrogen, the reaction is readily accomplished by contacting and mixing the dihalopyridine-2-carboxylic acid and the mercaptan in a suitable organic solvent, preferably dimethyl sulfoxide (DMSO), in the presence of a base, such as an alkali metal hydroxide at from about 100° C. to about 150° C. for a time sufficient (usually from about 1 to about 10 hours) to obtain the 3,6-bis(R-thio)pyridine-2-carboxylic acid salt or 5,6-bis(R-thio)pyridine-2-carboxylic acid salt.

The carboxylic acid salt formed by either of the procedures described above is converted to the corresponding acid utilizing conventional procedures, for example, by treating the carboxylic acid salt with an organic acid or mineral acid to give compounds of the formula:

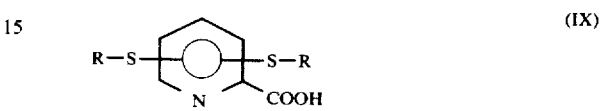

wherein the R—S— moieties are attached to the pyridine ring either at the 3 and 6 positions or 5 and 6 positions; and R has the same meaning as for formula I.

Although the use of different proportions of reactants is not detrimental to the above reactions, when $R_5$ is methyl, it is preferable to use about a 3:1 molar ratio of the mercaptan to the dihalo-pyridine-2-carboxylic acid methyl ester; and when $R_5$ is hydrogen, about a 2:1 molar ratio of the mercaptan to the dihalo-pyridine-2-carboxylic acid is preferred.

The bis(R-thio)pyridine-2-carboxylic acid described above is then decarboxylated to form a bis(R-thio)pyridine of the formula:

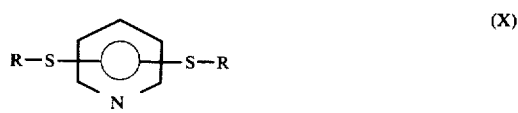

wherein the R—S— moieties are attached to the pyridine ring either at the 2 and 5 positions or 2 and 3 positions; and R is as defined for formula I.

Conventional procedures can be used for the above described decarboxylation. For example, the bis(R-thio)pyridine-2-carboxylic acid can be heated directly (often accompanied by reduced pressure as can be achieved in a Kügelrohr distillation apparatus) or heated in a suitable solvent employed as a heat transfer agent. Suitable solvents for use as heat transfer agents are, for example, decahydronaphthalene, xylene, 1,2-dichlorobenzene, diphenyl ether and other inert high boiling solvents. The choice of the procedure used for decarboxylation depends upon the properties of the compound to be decarboxylated. For example, the Kügelrohr distillation procedure requires that the bis(R-thio)pyridine-2-carboxylic acid be in a liquid state when decarboxylation is occurring, thus the decarboxylation temperature should fall between the melting point and the boiling point of the compound.

The bis(R-thio)pyridine is then oxidized to a bis(R-sulfonyl)pyridine of the formula:

wherein the phenoxypyridine compounds, which can be summarized as follows:

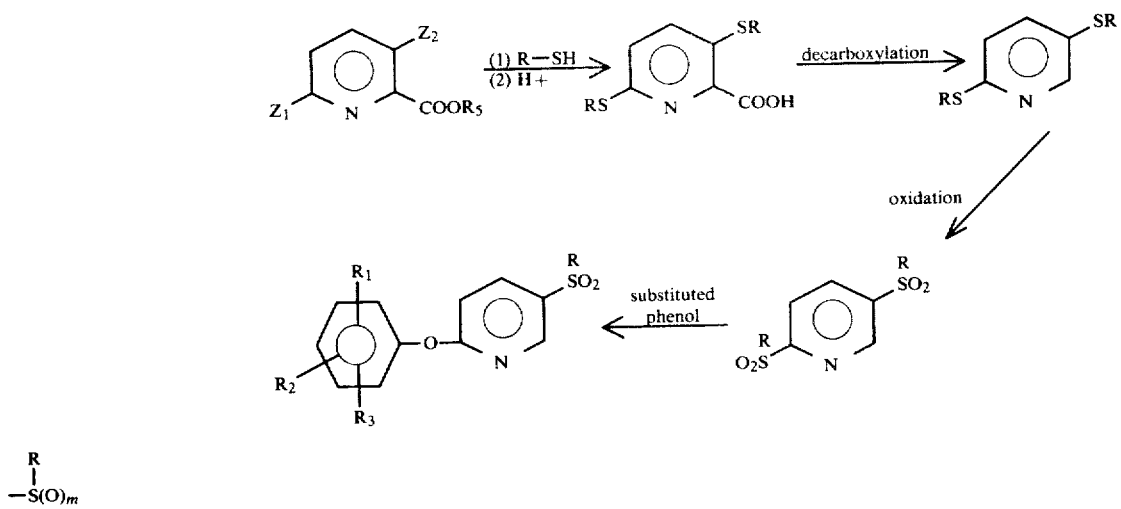

$$-\overset{R}{\underset{|}{S}}(O)_m$$

moieties are attached to the pyridine ring either at the 2 and 5 positions or 2 and 3 positions; and R is as defined as for formula I.

Considerations such as the solubility and reactivity of the bis(R-thio)pyridine and the ease of product recovery can dictate the choice of the most appropriate oxidizing agent and conditions to be employed for the oxidation. Oxidizing agents such as hydrogen peroxide/glacial acetic acid, hydrogen peroxide/trifluoroacetic acid, gaseous chlorine in aqueous media, m-chloroperbenzoic acid and other organic peracids and the like can be used for the oxidation.

The compound represented by formula XI (i.e., the 2,5-bis(R-sulfonyl)pyridine or 2,3-bis(R-sulfonyl)pyridine) is reacted with the appropriate substituted-phenol (i.e., those compounds represented by formula III) to form the desired 5-(R-sulfonyl)-2-phenoxypyridine or 3-(R-sulfonyl)-2-phenoxypyridine. The reaction of the bis(R-sulfonyl)pyridine and the substituted-phenol is conveniently accomplished by contacting and mixing the reactants in a suitable inert organic solvent in the presence of a base at a temperature of from about 40° C. to about 100° C. for a time sufficient to obtain the desired product. Usually a reaction time of about ½ to about 24 hours is sufficient to obtain a satisfactory yield of the product.

Suitable inert organic solvents are, for example, tetrahydrofuran (THF), 1,4-dioxane, 1,2-dimethoxyethane, isopropanol and other similar sec. and tert.-alcohols. In some cases a quantity of dimethyl sulfoxide may be included to facilitate the reaction. The base should be of sufficient basicity and in sufficient concentration to convert the phenol to its salt for reaction with the appropriate bis(R-sulfonyl)pyridine, such as potassium t.-butoxide, potassium carbonate and alkali metal hydroxides. The reactants can be combined in various proportions, however, the reactants are consumed in equimolar proportions and the use of approximately equimolar proportions is preferred. In some instances (for the less reactive compounds), it may be advantageous to combine and preheat the substituted-phenol and the base in the inert organic solvent prior to the addition of the bis(R-sulfonyl)pyridine.

The various steps of the above reaction sequence are exemplified by the preparation of the 5-(R-sulfonyl)-2-

Several other bis(R-sulfonyl)pyridine intermediates (i.e., 2,4-bis(R-sulfonyl)pyridines and 2,6-bis(R-sulfonyl)pyridines) can be employed to make compounds described herein.

The 2,4-bis(R-sulfonyl)pyridines and 2,6-bis(R-sulfonyl)pyridines can be prepared by reacting respectively a 2,4-dihalopyridine or 2,6-dihalopyridine (wherein each of the halo moieties is independently bromo, chloro, fluoro or iodo) with the appropriate mercaptan (i.e., the R-SH compound wherein R is defined as for formula I) under conditions sufficient to obtain the desired bis(R-thio) pyridine. The bis(R-thio)pyridine can then be oxidized to the bis(R-sulfonyl)pyridine utilizing the oxidation procedures previously described herein. The 2,4-bis(R-sulfonyl)pyridine or 2,6-bis(R-sulfonyl)pyridine can then be reacted with the substituted-phenol, i.e., the compound represented by formula III, employing the conditions described previously herein with regard to the reaction of the 2,5-bis(R-sulfonyl)pyridine or 2,3-bis(R-sulfonyl)pyridine with the substituted-phenol. The reaction of the 2,6-bis(R-sulfonyl)pyridine and the substituted-phenol gives the 6-(R-sulfonyl)-2-phenoxypyridine compounds.

There is a substantial advantage in employing a 2,5-bis(R-sulfonyl)pyridine, 2,3-bis(R-sulfonyl)pyridine or 2,6-bis(R-sulfonyl)pyridine in the reaction with the substituted-phenol, in that the respective products (i.e., 5-(R-sulfonyl)-2-phenoxypyridine, 3-(R-sulfonyl)-2-phenoxypyridine and 6-(R-sulfonyl)-2-phenoxypyridine) are obtained almost exclusively under the reaction conditions set forth herein. However, in the reaction of 2,4-bis(R-sulfonyl)pyridine with the substituted-phenol generally a mixture of 2-(R-sulfonyl)-4-phenoxypyridine and 4-(R-sulfonyl)-2-phenoxypyridine reaction products is formed, thus an additional separation step is required if the individual products are desired.

The various compounds described herein are recovered and purified using procedures well known in the art. Recovery procedures include, for example, dilution of the reaction mixture with water, filtration, decantation, centrifugation and extraction with appropriate solvents. Purification procedures include, for example, various chromatographic techniques, distillation (often at reduced pressure), washing and recrystallization.

The following examples are included to provide a better understanding of the invention but are not to be construed as a limitation thereon.

EXAMPLE 1

3,6-bis(methylthio)-2-pyridinecarboxylic acid

Methanethiol, (30.26 g) was dissolved in 200 milliliters (ml) of DMF that had been chilled in Dry Ice to below 0° C. To this solution was added 70.6 grams (g) of potassium t-butoxide (t-BuOK) while the temperature was maintained below 10° C. The resulting white slurry was added to a mixture of 39.35 g of methyl 3,6-dichloro-2-pyridinecarboxylate in 100 ml of DMF. The reaction was heated to 80° C. during the addition and after the addition was complete the temperature was raised to 100° C. and maintained there for 2 hours (hrs). Upon cooling the resulting paste was diluted with ether and filtered. The salts which were obtained were taken up in water, washed with $CH_2Cl_2$, and the aqueous phase made acidic with concentrated HCl to pH 3. The resulting solid was filtered and dried on a porous plate which gave 37 g (82% yield) of the crude product as a bright yellow solid. A portion of the crude product was recrystallized from ethanol, which gave purified 3,6-bis(methylthio)-2-pyridinecarboxylic acid as bright yellow plates, which was found to have a melting point (m.p.) of 142°–144° C.

EXAMPLE 2

2,5-bis(methylthio)pyridine

To 75 ml of decahydronaphthalene was added portionwise while heating 59.5 g of 3,6-bis(methylthio)-2-pyridinecarboxylic acid. When the mixture reached 155° C., gas bubbles began to appear. The reaction was heated at 175° C. until no more bubbles appeared. Upon cooling the decahydronaphthalene solution was treated with 40 ml of 6 normal (N) HCl in three portions resulting in the formation of a solid which was collected. The solid was covered with water. The aqueous layer and solid were then made basic with 50% NaOH and extracted with ether. The ether solution was treated with charcoal, dried and the ether removed, which gave 31 g (66% yield) of a yellow oil. A portion of this oil was placed on a Kügelrohr distillation apparatus and the product, 2,5-bis(methylthio)pyridine recovered, at 90° C. at a pressure of 0.1 mm Hg.

EXAMPLE 3

2,5-bis(methylsulfonyl)pyridine 2,5-bis(Methylthio)pyridine (26 g) was dissolved in 60 ml of acetic acid and 75 g of 30% hydrogen peroxide ($H_2O_2$) was added dropwise. After about ¼–⅓ of the oxidant had been added, the reaction exothermed to 95° C. Addition was stopped and the reaction was cooled to 75° C. with an ice bath. The addition was resumed and the temperature was kept at 75° C. for 4 hours. After cooling, the solid was recovered by filtration and then washed with water, ethanol and ether. A portion of the solid was recrystallized from acetonitrile which gave 2,5-bis(methylsulfonyl)pyridine as a white solid, m.p. 205°–207° C.

EXAMPLE 4

2,5-bis(ethylsulfonyl)pyridine

Sodium hydroxide (160 g) was weighed into a reaction flask, and covered with 1 liter (l) of DMSO which was then cooled in an ice bath (~10° C.) and then 149 g of ethanethiol was added. The mixture was stirred at room temperature for 1 hour and then 3,6-dichloro-2-pyridinecarboxylic acid (192 g) was added and the resulting mixture was heated at 130° C. for 6 hrs. After cooling, the reaction mixture was poured into 5 kilograms (kg) of ice, and acidified with 140 ml of concentrated HCl. A solid formed which was collected by filtration. The aqueous filtrate was decanted into a separatory funnel and extracted with 2 l of 1,1,1-trichloroethane. The solid was dissolved in 1 l of $CH_2Cl_2$. The organic solutions were combined, washed with 1 l of water, dried, and concentrated to give 273 g of crude 3,6-bis(ethylthio)-2-pyridinecarboxylic acid. The crude 3,6-bis(ethylthio)-2-pyridinecarboxylic acid was dissolved in 100 ml of 1,2-dichlorobenzene and added in small portions to 500 ml of 1,2-dichlorobenzene heated at 160° C. After the addition was complete, heating was continued for 2 hrs. The reaction mixture was chilled in ice and extracted three times with 200 ml of 6 N HCl.

The acidic solution was put in a large container equipped with a mechanical stirrer. To this fast stirring solution was added 4 l of 5.25% NaOCl solution. An off-white precipitate was formed which was collected by filtration, washed with water and dried to give 136.7 g of the product, 2,5-bis(ethylsulfonyl)pyridine, m.p. 148°–150° C.

EXAMPLE 5

2,5-bis((1-methylethyl)thio)pyridine

To 198 g of t-BuOK dissolved in 300 ml of DMF was added 2-propanethiol (163.47 ml) dropwise with an ice bath employed to keep the temperature below 50° C. As salt began to precipitate out an additional 50 ml of DMF was added. After addition was complete, the ice bath was removed and the mixture heated to 50° C. A solution of 100 g of methyl 3,6-dichloro-pyridine-2-carboxylate dissolved in DMF was added and the temperature during addition rose to 115° C. The temperature was then maintained at approximately 105°–110° C. until addition was completed and then the resulting mixture was heated at 100°–110° C. for 1¼ hrs. The reaction mixture was allowed to cool and the solvent removed in a rotary evaporator. The brown residue which remained was washed with ether and then dissolved in water. The solution was acidified with HCl, and the product, which oiled out, extracted with $CH_2Cl_2$. The $CH_2Cl_2$ was then removed using a rotary evaporator. Infrared spectroscopy (IR) and nuclear magnetic resonance spectroscopy (NMR) indicated that 3,6-bis((1-methylethyl)thio)-2-pyridinecarboxylic acid had formed. The 3,6-bis((1-methylethyl)thio)-2-pyridinecarboxylic acid was decarboxylated employing a Kügelrohr distillation apparatus, and 2,5-bis((1-methylethyl)thio)pyridine obtained, b.p. 310° C. (760 mm Hg).

EXAMPLE 6

2,5-bis((1-methylethyl)sulfonyl)pyridine

To 400 ml of trifluoroacetic acid was added 74.4 g of 2,5-bis((1-methylethyl)thio)pyridine and then temperature was raised to 54° C. The dropwise addition of 81.5 g of 30% aqueous $H_2O_2$ resulted in an exotherm to about 70°–75° C. followed by a rapid exotherm to 110° C. which was controlled by using an ice bath. After all of the peroxide had been added, the reaction mixture was heated at 55° C. for 40 minutes. Upon cooling the reaction mixture was poured into 700 ml of ice water which resulted in the formation of the product as a white solid. The solid was recovered by filtration and dried, which gave 83.4 g (87% yield) of 2,5-bis((1-methylethyl)sulfonyl)pyridine, m.p. 181° C.

EXAMPLE 7

3,6-bis(n-hexylthio)-2-pyridinecarboxylic acid

To 300 ml of DMSO was added 84.5 g of powdered NaOH with vigorous stirring followed by the addition of 150 g of n-hexyl mercaptan. The anion of the mercaptan was allowed to form and then 111 g of 3,6-dichloro-2-pyridinecarboxylic acid in 110 ml of DMSO was added through a dropping funnel. the temperature was increased during addition to 135° C. and maintained at that temperature for 2½ hours. Upon cooling the brown solution was poured into three volumes of water. The resulting solution was acidified with HCl and extracted with 1,1,1-trichloroethane. The organic layer was dried over $MgSO_4$ and the solvent removed on a rotary evaporator. The reaction yielded 155 g (68% yield) of 3,6-bis(n-hexylthio)-2-pyridinecarboxylic acid as a dark oil which solidified on standing; m.p. 40°–42° C.

EXAMPLE 8

2,5-bis(n-hexylthio)pyridine

Crude 3,6-bis(n-hexylthio)-2-pyridinecarboxylic acid (140 g) was placed on a Kügelrohr distillation apparatus and heated to 135°–145° C. which resulted in the material spontaneously losing $CO_2$. When gas evolution had ceased, the temperature was raised. The product distilled over at 185°–195° C. (0.2 mm Hg) and 98 g (82% yield) of the product 2,5-bis(n-hexylthio)pyridine recovered as an oil.

EXAMPLE 9

2,5-bis(n-hexylsulfonyl)pyridine

The compound, 2,5-bis(n-hexylsulfonyl)pyridine, m.p. 135°–136° C., was obtained by oxidizing 2,5-bis(n-hexylthio)pyridine using trifluoroacetic acid and 30% $H_2O_2$ employing substantially the same procedure set forth in the preparation of 2,5-bis((1-methylethyl)sulfonyl)pyridine.

EXAMPLE 10

3,6-bis(cyclohexylthio)-2-pyridinecarboxylic acid

The compound 3,6-bis(cyclohexylthio)-2-pyridinecarboxylic acid, m.p. 100°–101° C. was prepared by substantially the same procedure set forth for the preparation of 3,6-bis(ethylthio)-2-pyridinecarboxylic acid.

EXAMPLE 11

2,5-bis(cyclohexylthio)pyridine

The compound 2,5-bis(cyclohexylthio)pyridine was prepared by decarboxylating 3,6-bis(cyclohexylthio)-2-pyridinecarboxylic acid in a Kügelrohr distillation apparatus substantially as described in previous examples.

EXAMPLE 12

2,5-bis(cyclohexylsulfonyl)pyridine

The compound 2,5-bis(cyclohexylsulfonyl)pyridine, m.p. 213° C., was prepared by oxidizing 2,5-bis(cyclohexylthio)pyridine using trifluoroacetic acid and 30% $H_2O_2$ employing substantially the same procedure set forth for the preparation of 2,5-bis((1-methylethyl)sulfonyl)pyridine.

EXAMPLE 13

3,6-bis(phenylthio)-2-pyridinecarboxylic acid

In a raction flask 50 g of methyl 3,6-dichloro-pyridine-2-carboxylate and 100 ml of DMF were placed. In a beaker were placed 90 g of t-BuOK and 200 ml of DMF, followed by 88.3 g of thiophenol. The slurry which formed was added portionwise to the reaction flask resulting in a temperature rise. The resulting reaction mixture was heated at 110° C. for 3 hrs. The solvent was removed from the reaction mixture under reduced pressure and the residual solid was dissolved in water and washed with diethyl ether. The aqueous layer was acidified and 58 g of crude product obtained. A portion of the crude product was recrystallized from methanol and the recrystallized 3,6-bis(phenylthio)-2-pyridinecarboxylic acid found to have a melting point of 131°–132° C.

EXAMPLE 14

2,5-bis(phenylthio)pyridine

In a reaction flask was placed 100 ml of decahydronaphthalene which was then heated to 190° C. To the decahydronaphthalene was added 3,6-bis(phenylthio)-2-pyridinecarboxylic acid (51 g) in small portions. Heating was continued for 1 hour. After cooling, 60 ml of 6 N HCl was added resulting in the formation of a solid. The solid was collected and made alkaline with NaOH and extracted with diethyl ether. The organic layer was dried, concentrated and distilled using a Kügelrohr apparatus to give 37 g of 2,5-bis(phenylthio)pyridine, b.p. 190° C. (0.05 mm Hg).

EXAMPLE 15

2,5-bis(phenylsulfonyl)pyridine

The compound 2,5-bis(phenylsulfonyl)pyridine was prepared by oxidizing 2,5-bis(phenylthio)pyridine using glacial acetic acid and 30% $H_2O_2$ employing substantially the same procedure set forth for the preparation of 2,5-bis(methylsulfonyl)pyridine.

EXAMPLE 16

3,6-bis((phenylmethyl)thio)-2-pyridinecarboxylic acid

In 400 ml of DMF was dissolved 198 g of t-BuOK. While the temperature was kept at 70°–90° C. with cooling, 218.6 g of benzylmercaptan was added. To this mixture was added 100 g of methyl 3,6-dichloro-pyridine-2-carboxylate in 100 ml of DMF without cooling. The temperature rose to 105° C. and the temperature was maintained at 105° C. for 1 hr. The solvent was removed under reduced pressure and the residual solid obtained washed with diethyl ether. The solid was dissolved in water and allowed to stand overnight. Two layers were observed. The upper layer was acidified with concentrated HCl to a pH of about 1–2 resulting in the formation of a solid which was collected by filtration. NMR spectroscopy indicated a mno-substituted compound. The lower layer was acidified, which gave 86 g (48% yield) of a solid. The solid obtained from the lower layer was recrystallized from 2-propanol to give the product, 3,6-bis((phenylmethyl)thio)-2-pyridinecarboxylic acid, m.p. 129° C.

EXAMPLE 17

2,5-bis((phenylmethyl)thio)pyridine

In a flask, 150 ml of decahydronaphthalene was heated to 160°-170° C. with stirring. To this hot liquid was added 81 g of 3,6-bis((phenylmethyl)thio)-2-pyridinecarboxylic acid. After foaming subsided, heating was continued for another 20 minutes. After cooling, 37.7 g of product was obtained by filtration. The filtrate was diluted with 2-propanol and saturated with gaseous HCl to form the hydrochloride salt of the desired product. The hydrochloride was converted to the free base employing standard procedures to give a total of 70 g (99% yield) of the product, 2,5-bis((phenylmethyl)thio)pyridine, m.p. 77° C.

EXAMPLE 18

2,5-bis((phenylmethyl)sulfonyl)pyridine

The compound 2,5-bis((phenylmethyl)sulfonyl)pyridine, m.p. 265° C. (decomposition), was prepared by oxidizing 2,5-bis((phenylmethyl)thio)pyridine using procedures previously described herein.

EXAMPLE 19

2,4-bis(methylthio)pyridine

Sodium hydroxide (20.8 g) was suspended in 200 ml DMF, and cooled to <5° C. Methylthiol (25 g) was added and stirred under a Dry-Ice condenser until all the NaOH dissolved. 2,4-Dichloropyridine (35 g) was then added and an exotherm was observed (>70° C.). The resulting reaction mixture was heated at 140° C. for 6 hours. After cooling, the reaction mixture was poured into 400 g of ice and extracted with $CH_2Cl_2$. The organic layer was dried and concentrated and a yellow liquid obtained which was distilled under reduced pressure. The third fraction obtained, at 99° C./0.05 mm Hg, contained 35.4 g of the desired product, 2,4-bis(methylthio)pyridine.

EXAMPLE 20

2,4-bis(methylsulfonyl)pyridine

The product 2,4-bis(methylsulfonyl)pyridine was prepared by oxidizing 2,4-bis(methylthio)pyridine employing a sodium hypochlorite solution, using substantially the same procedure described previously herein.

Employing procedures substantially as described herein, the following compounds were prepared:

EXAMPLE 21

2,3-bis(methylsulfonyl)pyridine, m.p. 175°-176.5° C.

EXAMPLE 22

5,6-bis(ethylthio)-2-pyridinecarboxylic acid, m.p. 112°-113° C.

EXAMPLE 23

2,3-bis(ethylthio)pyridine, b.p. 95° C./0.3 mm Hg.

EXAMPLE 24

2,3-bis(ethylsulfonyl)pyridine, m.p. 132° C.

EXAMPLE 25

2,6-bis(methylthio)pyridine.

EXAMPLE 26

2,6-bis(methylsulfonyl)pyridine, m.p. 196°-199.5° C.

The physical properties of the above examples are summarized in Table 1. The respective m, R and A substituents listed in Table I are determined by reference to formula VII.

TABLE 1

| Compound Example Number | R | m | A | M.p. °C.* B.p. (mm Hg) | Calculated % C | Calculated % H | Calculated % N | Found % C | Found % H | Found % N |
|---|---|---|---|---|---|---|---|---|---|---|
| 1 | 3,6-$CH_3$ | 0 | 2-COOH | 142–144 | 44.63 | 4.21 | 6.51 | 44.58 | 4.22 | 6.42 |
| 2 | 2,5-$CH_3$ | 0 | H | 90 (0.1) | 49.08 | 5.30 | 8.18 | 49.78 | 5.35 | 8.04 |
| 3 | 2,5-$CH_3$ | 2 | H | 205–207 | 35.73 | 3.86 | 5.95 | 35.91 | 3.97 | 5.98 |
| 4 | 2,5-$C_2H_5$ | 2 | H | 148–150 | 41.05 | 4.97 | 5.32 | 40.63 | 5.02 | 5.33 |
| 5 | 2,5-$(CH_3)_2CH$ | 0 | H | 310 (760) | 58.10 | 7.54 | 6.16 | 57.10 | 7.01 | 6.18 |
| 6 | 2,5-$(CH_3)_2CH$ | 2 | H | 181 | 45.34 | 5.88 | 4.81 | 45.47 | 5.88 | 4.73 |
| 7 | 3,6-$CH_3(CH_2)_5$ | 0 | 2-COOH | 40–42 | 60.80 | 8.22 | 3.94 | 58.62 | 7.96 | 3.60 |
| 8 | 2,5-$CH_3(CH_2)_5$ | 0 | H | 185–195 (0.2) | 65.54 | 9.38 | 4.50 | 64.22 | 9.03 | 4.31 |
| 9 | 2,5-$CH_3(CH_2)_5$ | 2 | H | 135–136 | 54.37 | 7.78 | 3.73 | 54.13 | 7.77 | 3.70 |
| 10 | 3,6-cyclohexyl | 0 | 2-COOH | 100–101 | 61.50 | 7.17 | 3.99 | 61.09 | 7.26 | 4.29 |
| 11 | 2,5-cyclohexyl | 0 | H | 177–190 (0.5) | 66.39 | 8.19 | 4.56 | 65.49 | 7.97 | 4.13 |
| 12 | 2,5-cyclohexyl | 2 | H | 213 | 54.96 | 6.78 | 3.77 | 54.80 | 6.93 | 3.91 |
| 13 | 3,6-phenyl | 0 | 2-COOH | 131–132 | 63.69 | 3.86 | 4.13 | 63.32 | 3.96 | 4.05 |
| 14 | 2,5-phenyl | 0 | H | 190 (0.05) | 69.12 | 4.43 | 4.74 | 68.64 | 4.51 | 4.82 |
| 15 | 2,5-phenyl | 2 | H | 202–205 | 56.81 | 3.64 | 3.90 | 56.88 | 3.75 | 3.99 |
| 16 | 3,6-benzyl | 0 | 2-COOH | 129 | 65.37 | 4.66 | 3.81 | 64.99 | 4.85 | 3.65 |
| 17 | 2,5-benzyl | 0 | H | 77 | 70.55 | 5.30 | 4.33 | 70.49 | 5.32 | 4.33 |
| 18 | 2,5-benzyl | 2 | H | 265 (d)** | 58.89 | 4.42 | 3.62 | 58.29 | 4.52 | 3.57 |
| 19 | 2,4-$CH_3$ | 0 | H | 99 (0.05) | 49.08 | 5.30 | 8.18 | 48.72 | 5.29 | 8.22 |
| 20 | 2,4-$CH_3$ | 2 | H | 167–168 | 35.73 | 3.86 | 5.95 | 35.86 | 3.79 | 6.03 |
| 21 | 2,3-$CH_3$ | 2 | H | 175–176.5 | 35.73 | 3.86 | 5.95 | 35.35 | 3.80 | 5.68 |
| 22 | 5,6-$C_2H_5$ | 0 | 2-COOH | 112–113 | 49.35 | 5.38 | 5.76 | 49.24 | 5.53 | 5.66 |
| 23 | 2,3-$C_2H_5$ | 0 | H | 95 (0.3) | 54.23 | 6.57 | 7.03 | 54.11 | 6.48 | 7.00 |
| 24 | 2,3-$C_2H_5$ | 2 | H | 132 | 41.05 | 4.97 | 5.32 | 41.08 | 5.06 | 5.29 |
| 25 | 2,6-$CH_3$ | 0 | H | IDENTIFIED BY NMR | | | | | | |
| 26 | 2,6-$CH_3$ | 2 | H | 196–199.5 | IDENTIFIED BY NMR | | | | | |

*The values presented refer to either the melting point in degrees Centigrade or the boiling point in degrees Centigrade at a particular pressure indicated in millimeters of mercury.
**The symbol "(d)" means that the compound decomposed at the indicated temperature.

EXAMPLE 27

5-(methylsulfonyl)-2-(4-((trifluoromethyl)thio)phenoxy)pyridine

To 4.95 g of 4-(trifluoromethylthio)phenol dissolved in a 20 ml THF/20 ml DMSO mixture was added 2.9 g of t-BuOK and then 6.0 g of 2,5-bis(methylsulfonyl) pyridine, and the resulting mixture heated at 58° C. for 1½ hrs. The reaction mixture was cooled to room temperature and added to approximately 3 to 4 volumes of water. The yellow-brown precipitate that formed was removed by filtration and then recrystallized from $CH_2Cl_2$/ethanol. The purified product, 5-(methylsulfonyl)-2-(4-((trifluoromethyl)thio)phenoxy)pyridine, (60% yield), was recovered as tiny cream-white plates, m.p. 134°–135° C.

EXAMPLE 28

5-(methylsulfonyl)-2-(4-phenoxyphenoxy)pyridine

To 4.75 g of 4-phenoxyphenol dissolved in a 20 ml THF/20 ml DMSO mixture was added 2.9 g of t-BuOK and then 6.0 g of 2,5-bis(methylsulfonyl)pyridine, and the resulting mixture heated at 58° C. for 1½ hrs. The reaction mixture was cooled overnight and then poured into 200 ml of water and stirred. A pink-white solid precipitated which was recovered and then dried on a porous plate. Recrystallization and ethanol/$CH_2Cl_2$ gave purified 5-(methylsulfonyl)-2-(4-phenoxyphenoxy)pyridine, (88% yield), as slightly pink shiny plates, m.p. 136.5°–138° C.

EXAMPLE 29

2-(4-bromophenoxy)-5-(methylsulfonyl)pyridine

To 18.4 g of 4-bromophenol dissolved in a 80 ml THF/80 ml DMSO mixture was added 13.1 g of t-BuOK and then 25.0 g of 2,5-bis(methylsulfonyl)pyridine, and the resulting mixture heated at 58° C. for 1½ hrs. The reaction mixture was cooled overnight and then poured into 3 volumes of water and stirred. The pink-white crystalline product was filtered, dissolved in $CH_2Cl_2$ and dried over $MgSO_4$. Recrystallization from ethanol gave purified 2-(4-bromophenoxy)-5-(methylsulfonyl)pyridine, (55% yield), as white shiny needles, m.p. 125°–126° C.

EXAMPLE 30

4-((5-(methylsulfonyl)-2-pyridinyl)oxy)benzonitrile

To 3.04 g of 4-cyanophenol dissolved in a 15 ml THF/15 ml DMSO mixture was added 2.86 g of t-BuOK and then 6 g of 2,5-bis(methylsulfonyl)pyridine, and the resulting mixture heated at 60° C. for 1½ hrs. After cooling, the reaction mixture was poured into water and the solid which formed collected. Recrystallization from acetonitrile gave purified 4-((5-(methylsulfonyl)-2-pyridinyl)oxy)benzonitrile, m.p. 195°–196° C.

EXAMPLE 31

(4-((5-(methylsulfonyl)-2-pyridinyl)oxy)phenyl)phenylmethanone

To 5.5 g of p-hydroxybenzophenone in a 25 ml THF/25 ml DMSO mixture was added 3.6 g of t-BuOK and then 6.51 g of 2,5-bis(methylsulfonyl)pyridine, and the resulting mixture was heated at 62° C. for 1½ hrs. The reaction mixture was cooled and added to approximately 3 to 4 volumes of water and stirred. The crude product which formed was filtered and dried. Recrystallization from ethanol gave purified (4-((5-(methylsulfonyl)-2-pyridinyl)oxy)phenyl)phenylmethanone, m.p. 130°–131.5° C.

Other 2-(substituted-phenoxy)-5-(methylsulfonyl)-pyridines were prepared by reacting the appropriate substituted-phenol and 2,5-bis(methylsulfonyl)pyridine utilizing substantially the same procedures described above. The compounds which were prepared follow:

EXAMPLE 32

2-(4-chlorophenoxy)-5-(methylsulfonyl)pyridine, m.p. 117°–118° C.

EXAMPLE 33

2-(4-(1,1-dimethylethyl)phenoxy)-5-(methylsulfonyl)pyridine, m.p. 142° C.

EXAMPLE 34

1-(4-((5-(methylsulfonyl)-2-pyridinyl)oxy)phenyl)ethanone, m.p. 143°–144° C.

EXAMPLE 35

2-(3-bromophenoxy)-5-(methylsulfonyl)pyridine, m.p. 134.5° C.

EXAMPLE 36

3-((5-(methylsulfonyl)-2-pyridinyl)oxy)benzonitrile, m.p. 139° C.

EXAMPLE 37

2-(4-(methylthio)phenoxy)-5-(methylsulfonyl)pyridine, m.p. 128°–130° C.

EXAMPLE 38

2-(3,4-dichlorophenoxy)-5-(methylthio)pyridine (a) Preparation of 2-(3,4-dichlorophenoxy)-5-nitropyridine intermediate To 44.9 g of t-BuOK in 250 ml of DMSO was added 65.2 g of 3,4-dichlorophenol in 50 ml of DMSO causing a temperature rise to between 65°–70° C. To this warm solution was added 2-chloro-5-nitropyridine (63.4 g) which raised the temperature to 90° C. The mixture was stirred without heating until the temperature dropped to 40° C. (~1 hr). The reaction mixture was poured into 1 kilogram (kg) of ice-water and the solid collected by filtration. The solid was dissolved in $CH_2Cl_2$, dried over $Na_2CO_3$, treated with charcoal, redried over $MgSO_4$ and then filtered. The $CH_2Cl_2$ solution was concentrated to 250 ml, then diluted to 700 ml with hexane and allowed to stand overnight. From this solution, a crystalline material was collected by filtration and 94.8 g of 2-(3,4-dichlorophenoxy)-5-nitropyridine obtained, m.p. 101°–102.5° C.

(b) Preparation of 2-(3,4-dichlorophenoxy)-5-pyridinamine intermediate

The 2-(3,4-dichlorophenoxy)-5-nitropyridine described above was divided into 4 portions of 23.7 g each, and each portion was then hydrogenated in absolute ethanol employing a palladium catalyst as well known in the art. After removal of the catalyst, the ethanol filtrates were combined and evaporated to dryness. The residue which remained was diluted with isopropyl alcohol and hexane and then chilled. The resulting solid was collected by filtration and vacuum dried to give 70.8 g of 2-(3,4-dichlorophenoxy)-5- pyridinamine as a rose colored powder, m.p. 78°–79.3° C.

(c) Preparation of 2-(3,4-dichlorophenoxy)-5-(methylthio)pyridine, as described in Method I To acetonitrile (200 ml) was added 4.0 g of NaOH and the mixture chilled to less than 5° C. To the chilled mixture 4.8 g of methanethiol was added and the mixture stirred under a Dry-Ice condenser for 1 hr.

The 2-(3,4-dichlorophenoxy)-5-pyridinamine was mixed with HBF$_4$ (~25.1 g) in ethanol and cooled to 0° C. and then NaNO$_2$ (7.6 g) in 20 ml of water was added slowly, maintaining the temperature below 5° C. After the addition was completed, 100 ml of diethyl ether was added to the paste, then the paste was stirred. The paste was filtered and the major portion of the solvent removed. The filter cake which was obtained from the filtration was added to the CH$_3$SNa solution (at 15° C.) described above in small portions and the mixture warmed carefully to 20° C. After the addition was complete, the mixture was stirred at room temperature overnight, MgSO$_4$ was added and then the solution was filtered. The filtrate was concentrated under reduced pressure to a semisolid which was extracted with CH$_2$Cl$_2$. The CH$_2$Cl$_2$ solution was dried and concentrated and 25 g of a red syrup obtained. The red syrup was distilled on a Kügelrohr distillation apparatus and the lower boiling cut (~2 g) discarded. The major fraction (14.1 g) obtained from the distillation was further purified on a Water's Prep LC 500 instrument with 5% ethyl acetate in hexane employed as the eluent. The product, 2-(3,4-dichlorophenoxy)-5-(methylthio)pyridine, (11 g), was obtained as a yellow oil.

(d) Preparation of 2-(3,4-dichlorophenoxy)-5-(methylthio)pyridine, as described in Method II.

2-(3,4-Dichlorophenoxy)-5-pyridinamine (20 g) was diazotized employing substantially the same procedure previously described herein. The diazonium salt was added portion-wise to a solution of 17.5 g of potassium ethyl xanthate in 50 ml of water at 60° C. More xanthate was added periodically to account for the neutralization of the acidic diazonium solution and a red oil separated. After the addition of the diazonium salt was complete and the reaction mixture had cooled to room temperature, the red oil was taken up in CH$_2$Cl$_2$. The aqueous layer was extracted with CH$_2$Cl$_2$. The extracts were combined and washed once with 10% NaOH and then washed several times with water. After drying over MgSO$_4$, the solvent was removed leaving the xanthate compound as a residue, which was used as is in the next step. The xanthate compound (18 g) was dissolved in 55 ml of CH$_2$Cl$_2$ and 7.0 g of a 70% solution of ethylamine added. The resulting mixture was stirred at room temperature for 2 hrs and then concentrated HCl (excess) was added to neutralize the base. The organic layer was removed, dried over MgSO$_4$, and then filtered. Ethyl alcohol (50 ml) was added and most of the CH$_2$Cl$_2$ was removed. The alcohol solution was then treated with 3.35 g of 85% KOH and 5 ml of methyl iodide. The mixture was stirred 2 hrs at room temperature and then the solvent was removed leaving a residue. The residue was extracted with CH$_2$Cl$_2$ and then washed with water. The CH$_2$Cl$_2$ was dried and evaporated and the material that was obtained was purified using a Water's Prep LC 500 instrument employing a mixture of 10% acetone in hexane as the eluent. A final purification was accomplished using a Kügelrohr distillation apparatus and the product, 2-(3,4-dichlorophenoxy)-5-(methylthio)pyridine, collected at 145° C. at about 0.05 mm of Hg.

EXAMPLE 39

2-(3,4-dichlorophenoxy)-5-(methylsulfinyl)pyridine

In 110 ml of water was dissolved 7.06 g of sodium metaperiodate. The solution was diluted with 500 ml of methanol and cooled to 15° C. A solution of 9.35 g of 2-(3,4-dichlorophenoxy)-5-(methylthio)pyridine in 125 ml of methanol was added. The resulting mixture was stirred at room temperature for 3 days. The solid was removed by filtration and the filtrate concentrated to approximately 100 ml. The concentrated filtrate was extracted with CH$_2$Cl$_2$ and the CH$_2$Cl$_2$ solution dried and concentrated to obtain 16.5 g of a yellow oil. The oil solidified when chilled under hexane. The solid was recrystallized from CH$_2$Cl$_2$/hexane to give 7.9 g, (80% yield), of 2-(3,4-dichlorophenoxy)-5-(methylsulfinyl)pyridine, as off-white crystals, m.p. 88°–90° C.

EXAMPLE 40

2-(3,4-dichlorophenoxy)-5-(methylsulfonyl)pyridine

To 3,4-dichlorophenol (13.8 g) dissolved in a 60 ml THF/60 ml DMSO mixture was added 9.5 g of t-BuOK. The temperature rose to about 40° C. and then 19.8 g of 2,5-bis(methylsulfonyl)pyridine was added. The reaction mixture was warmed to 50° C. and the temperature maintained at 50° C. for 1 hour. The reaction mixture was cooled, poured into approximately 3 volumes of water and the solid collected. The solid was dried on a porous plate and then recrystallized from CH$_2$Cl$_2$/ethanol to give 23.5 g of 2-(3,4-dichlorophenoxy)-5-(methylsulfonyl)pyridine as shiny white plates, m.p. 120°–121° C.

EXAMPLE 41

5-(ethylsulfonyl)-2-(3,4-methylenedioxyphenoxy)pyridine

Into a reaction flask was weighed 5.6 g of t-BuOK and then 50 ml of THF was added. In 50 ml of DMSO was dissolved 6.2 g of 3,4-methylenedioxyphenol which was then slowly added to the t-BuOK solution with stirring. To the resulting potassium phenate solution was added 10.5 g of 2,5-bis(ethylsulfonyl)pyridine and this mixture heated at 50°–55° C. for 3 hrs. After cooling, the reaction mixture was poured into 400 g of ice, stirred and then filtered. The solid which was recovered was dissolved in CH$_2$Cl$_2$, treated with charcoal, dried over MgSO$_4$ and then filtered. The CH$_2$Cl$_2$ solution was concentrated to 50 ml, diluted with an equal volume of hexane and then chilled and a crystalline material recovered, which provided 9.9 g, (80% yield), of 5-ethylsulfonyl-2-(3,4-methylenedioxyphenoxy)pyridine, m.p. 97°–99° C.

Other 2-(substituted-phenoxy)-5-(ethylthio or ethylsulfinyl or ethylsulfonyl)pyridines were prepared according to the procedures described herein. The compounds which were prepared follow:

EXAMPLE 42

2-(4-chlorophenoxy)-5-(ethylsulfonyl)pyridine, m.p. 128°–130° C.

EXAMPLE 43

(4-((5-(ethylsulfonyl)-2-pyridinyl)oxy)phenyl)-phenylmethanone, m.p. 131°–132° C.

EXAMPLE 44

5-(ethylsulfonyl)-2-(4-phenoxyphenoxy)pyridine, m.p. 38°–41° C.

EXAMPLE 45

2-(3,4-dichlorophenoxy)-5-(ethylthio)pyridine, b.p. 145° C. at 0.05 mm of Hg.

EXAMPLE 46

2-(3,4-dichlorophenoxy)-5-(ethylsulfinyl)pyridine, m.p. 80°–82° C.

EXAMPLE 47

2-(3,4-dichlorophenoxy)-5-(ethylsulfonyl)pyridine

To 6.7 g of t-BuOK in a mixture of 50 ml of THF and 50 ml of DMSO was added 8.2 g of 3,4-dichlorophenol and then 7.9 g of 2,5-bis(ethylsulfonyl)pyridine, and the resulting mixture heated at 55° C. for 3 hrs. The reaction mixture was cooled and then poured into ice-water. A precipitate formed which was collected by filtration and then washed with water. The recovered solid was then dissolved in $CH_2Cl_2$ and dried over $MgSO_4$. The solution was diluted with an equal volume of hexane and treated with silica gel and then filtered. The solution was then concentrated to 50 ml, cooled and 6.5 g of 2-(3,4-dichlorophenoxy)-5-ethylsulfonyl)pyridine recovered as a white powder, m.p. 117°–118° C.

EXAMPLE 48

5-(ethylsulfonyl)-2-(2,4,5-trichlorophenoxy)pyridine

In 70 ml of sulfolane were mixed 10.5 g of 2,5-bis(ethylsulfonyl)pyridine, 15.8 g of 2,4,5-trichlorophenol and 11.06 g of potassium carbonate. The mixture was warmed gradually to 170° C. and maintained at that temperature for 2 hrs. The reaction mixture was cooled and then poured into 300 g of ice containing 4 g of sodium hydroxide. The aqueous solution was extracted with ether. The organic layer was washed with water, dried over $MgSO_4$ and concentrated. The product was purified using a Water's Prep LC 500 instrument with 10% ethyl acetate/90% hexane as eluent. Recrystallization from diethyl ether gave 2.8 g, (19% yield), of purified 5-(ethylsulfonyl)-2-(2,4,5-trichlorophenoxy)pyridine, m.p. 120°–122° C.

EXAMPLE 49

2-(3,4-dichlorophenoxy)-5-((1-methylethyl)sulfonyl)pyridine

To 4.89 g of 3,4-dichlorophenol dissolved in a 25 ml THF/25 ml DMSO mixture was added 3.2 g of t-BuOK and then 8.74 g of 2,5-bis((1-methylethyl)sulfonyl)pyridine, and the resulting mixture was heated at 58° C. for 1½ hrs. The reaction mixture was allowed to cool overnight and then poured in approximately 3 to 4 volumes of water and stirred. The yellow-white precipitate which formed was removed by filtration. Recrystallization from $CH_2Cl_2$/ethanol gave the product, 2-(3,4-dichlorophenoxy)-5-((1-methylethyl)sulfonyl)pyridine, (42% yield), as tiny white needles, m.p. 91°–92° C.

Other 2-(substituted-phenoxy)-5-((1-methylethyl)sulfonyl)pyridines were prepared by reacting the appropriate substituted-phenol and 2,5-bis((1-methylethyl)sulfonyl)pyridine utilizing substantially the same procedure set forth for the preparation of 2-(3,4-dichlorophenoxy)-5-((1-methylethyl)sulfonyl)pyridine. The compounds which were prepared follow:

EXAMPLE 50

2-(4-bromophenoxy)-5-((1-methylethyl)sulfonyl)pyridine, m.p. 93°–94° C.

EXAMPLE 51

(4-((5-((5-((1-methylethyl)sulfonyl)-2-pyridinyl)oxy)-phenyl)phenylmethanone, m.p. 113°–114° C.

EXAMPLE 52

1-(4-((5-((1-methylethyl)sulfonyl)-2-pyridinyl)oxy)-phenyl)ethanone, m.p. 114°–115° C.

EXAMPLE 53

2-(4-bromophenoxy)-5-(n-hexylsulfonyl)pyridine

To 4.33 g of 4-bromophenol dissolved in a 22 ml THF/22 ml DMSO mixture was added 3.1 g of t-BuOK and then 9.39 g of 2,5-bis(n-hexylsulfonyl)pyridine, and the resulting mixture heated at 59° C. for 1 hr. The reaction mixture was cooled to room temperature and then added to approximately 4 to 5 volumes of water. The yellow precipitate which formed was removed by filtration. Recrystallization from $CH_2Cl_2$/ethanol gave the product, 2-(4-bromophenoxy)-5-(n-hexylsulfonyl)-pyridine, (52% yield), as white shiny prisms, m.p. 94° C.

Other 2-(substituted-phenoxy)-5-(n-hexylsulfonyl)pyridines were prepared by reacting the appropriate substituted-phenol and 2,5-bis(n-hexylsulfonyl)pyridine utilizing substantially the same procedure set forth for the preparation of 2-(4-bromophenoxy)-5-(n-hexylsulfonyl)pyridine. The compounds which were prepared follow:

EXAMPLE 54

2-(3,4-dichlorophenoxy)-5-(n-hexylsulfonyl)pyridine, m.p. 75.5° C.

EXAMPLE 55

(4-((5-(n-hexylsulfonyl)-2-pyridinyl)oxy)phenyl)-phenylmethanone, m.p. 72°–74° C.

EXAMPLE 56

1-(4-((5-(cyclohexylsulfonyl)-2-pyridinyl)oxy)phenyl)ethanone

To 3.68 g of p-hydroxyacetophenone in a 25 ml THF/25 ml DMSO mixture was added 3.2 g of t-BuOK and then 10.03 g of 2,5-bis(cyclohexylsulfonyl)pyridine, and the resulting mixture was heated at 62° C. for 1½ hrs. The reaction mixture was cooled overnight, then added to 4 volumes of water and the crude product which formed recovered by filtration. Recrystallization of the crude product from $CH_2Cl_2$/ethanol gave the product, 1-(4-((5-(cyclohexylsulfonyl)-2-pyridinyl)oxy)phenyl)ethanone, (31% yield), as light yellow prisms, m.p. 116°–118° C.

Other 2-(substituted-phenoxy)-5-(cyclohexylsulfonyl)pyridines were prepared by reacting the appropriate substituted-phenol and 2,5-bis(cyclohexylsulfonyl)pyridine utilizing substantially the same procedure set forth for the preparation of 1-(4-((5-(cyclohexylsulfonyl)-2-pyridinyl)oxy)phenyl)ethanone. The compounds which were prepared follow:

EXAMPLE 57

2-(4-bromophenoxy)-5-(cyclohexylsulfonyl)pyridine, m.p. 146.5°–147° C.

EXAMPLE 58

2-(3,4-dichlorophenoxy)-5-(cyclohexylsulfonyl)pyridine, m.p. 114° C.

EXAMPLE 59

(4-((5-(cyclohexylsulfonyl)-2-pyridinyl)oxy)phenyl)phenylmethanone, m.p. 138°–139° C.

EXAMPLE 60

2-(3,4-dichlorophenoxy)-5-(phenylsulfonyl)pyridine

To 4.08 g of 3,4-dichlorophenol dissolved in a 25 ml THF/25 ml DMSO mixture was added 2.9 g of t-BuOK and then 8.99 g of 2,5-bis(phenylsulfonyl)pyridine, and the resulting mixture heated at 58° C. for 1½ hrs. The reaction mixture was cooled to room temperature, then added to 3 to 4 volumes of water and stirred. The brown precipitate which formed was removed by filtration. Recrystallization from $CH_2Cl_2$/ethanol gave the purified product, 2-(3,4-dichlorophenoxy)-5-(phenylsulfonyl)pyridine, (68% yield), as white shiny needles, m.p. 113°–114° C.

Another 2-(substituted-phenoxy)-5-(phenylsulfonyl)pyridine was prepared using substantially the same procedures described herein. The compound which was prepared follows:

EXAMPLE 61

2-(4-bromophenoxy)-5-(phenylsulfonyl)pyridine, m.p. 120°–121° C.

EXAMPLE 62 phenyl(4-((5-phenylmethyl)sulfonyl)-2-pyridinyl)oxy)phenyl)methanone

To 4.96 g of p-hydroxybenzophenone in a 25 ml THF/25 ml DMSO mixture was added 3.1 g of t-BuOK and then 9.69 g of 2.5-bis((phenylmethyl)sulfonyl)pyridine and the resulting mixture heated at 60° C. for 1½ hrs. The reaction mixture was allowed to cool overnight, diluted with 4 volumes of water, and the golden-brown precipitate which formed removed by filtration. Recrystallization from $CH_2Cl_2$/ethanol and then from toluene gave the product, phenyl(4-((5-((phenylmethyl)sulfonyl)-2-pyridinyl)oxy)phenyl)methanone, (44% yield), as tan prisms, m.p. 146°–147° C.

Other 2-(substituted-phenoxy)-5-((phenylmethyl)sulfonyl)pyridines were prepared according to the procedures described herein. The compounds which were prepared follow:

EXAMPLE 63

2-(3,4-dichlorophenoxy)-5-((phenylmethyl)sulfonyl)pyridine, m.p. 112°–113° C.

EXAMPLE 64

2-(4-bromophenoxy)-5-((phenylmethyl)sulfonyl)pyridine, m.p. 130° C.

Example 65 and Example 66 were prepared in a single reaction as follows:

EXAMPLE 65

2-(3,4-dichlorophenoxy)-4-(methylsulfonyl)pyridine.

EXAMPLE 66

4-(3,4-dichlorophenoxy)-2-(methylsulfonyl)pyridine

Potassium t-butoxide (7.86 g) was weighed into a reaction flask and covered with 50 ml of THF. 3,4-Dichlorophenol (11.41 g) was dissolved in 50 ml of DMSO and added to the flask followed by the addition of 14.12 g of 2,4-bis(methylsulfonyl)pyridine. The reaction mixture was heated at 50° C. for 10 hours, cooled and then poured into 600 g of ice. An oil formed and it was extracted into 1,1,1-trichloroethane. The organic solution was dried over $K_2CO_3$, treated with charcoal, redried with $MgSO_4$ and concentrated. Purification of the residue on a Water's Prep LC 500 instrument using a mixture of 20:80 ethyl acetate-hexane as the eluent gave two components.

Component A was distilled on a Kügelrohr distillation apparatus and the fraction collected at 155°–160° C./0.05 mm Hg was determined to be 2-(3,4-dichlorophenoxy)-4-(methylsulfonyl)pyridine by nuclear magnetic resonance (NMR) spectroscopy. The oil which was collected solidified on standing and the product, 2-(3,4-dichlorophenoxy)-4-(methylsulfonyl)pyridine found to have a melting point of 95°–96° C.

Component B was distilled on a Kügelrohr distillation apparatus and a light yellow oil obtained. The oil was recrystallized from hexane/$CH_2Cl_2$ to give 3.5 g of crystalline material, m.p. 91°–93° C. The crystalline material was determined to be 4-(3,4-dichlorophenoxy)-2-(methylsulfonyl)pyridine by NMR spectroscopy.

Other subject compounds were prepared according to the procedures set forth herein. The compounds which were prepared follow:

EXAMPLE 67

2-(3,4-dichlorophenoxy)-6-(methylsulfonyl)pyridine, m.p. 90°–91° C.

EXAMPLE 68

(4-((6-methylsulfonyl)-2-pyridinyl)oxy)phenyl)phenylmethanone, m.p. 143°–144° C.

EXAMPLE 69

2-(methylsulfonyl)-6-(4-(phenylmethyl)phenoxy)pyridine, b.p. 200° C./0.1 mm Hg.

EXAMPLE 70

2-(4-bromophenoxy)-6-(methylsulfonyl)pyridine, m.p. 81°–82° C.

EXAMPLE 71

2-(3,4-dichlorophenoxy)-3-(methylsulfonyl)pyridine

Potassium t-butoxide (2.47 g) was dissolved in 30 ml of THF and then 3.46 g of 3,4-dichlorophenol dissolved in THF was added. A solution of 5.00 g of 2,3-bis(methylsulfonyl)pyridine in 20 ml THF/20 ml DMSO was added dropwise. The resulting mixture was stirred at room temperature for 3 hours. The reaction mixture was poured onto ice-water which resulted in the formation of an oil which solidified on standing. The product was collected by filtration and dried in a vacuum oven and 5.33 g of material obtained. Recrystallization from $CH_2Cl_2$/hexane gave purified 2-(3,4-dichlorophenoxy)-3-(methylsulfonyl)pyridine, m.p. 95°–96° C.

Other subject compounds were prepared according to the procedures set forth herein. The compounds which were prepared follow:

EXAMPLE 72

(4-((3-(methylsulfonyl)-2-pyridinyl)oxy)phenyl)-phenylmethanone, m.p. 119°-120° C.

EXAMPLE 73

2-(3,4-dichlorophenoxy)-3-(ethylsulfonyl)pyridine, m.p. 82° C.

EXAMPLE 74

4-((3-(ethylsulfonyl)-2-pyridinyl)oxy)phenyl)phenylmethanone, m.p. 149° C.

EXAMPLE 75

3-(3,4-dichlorophenoxy)-5-(methylthio)pyridine

In 250 ml of DMF was dissolved 46.60 g of 2-cyano-3,5-dichloropyridine, which was then cooled to −25° C. with stirring under $N_2$. Methanethiol (18.0 ml) was added. To the above mixture 43.13 g of 1,8-diazabicyclo[5.4.0]undec-7-ene was added dropwise at a rate sufficient to maintain the temperature below −20° C. and the resulting reaction mixture stirred for 30 minutes. The reaction mixture was poured onto 1500 ml of ice and the solid collected. The solid was dried briefly on a porous plate, then vacuum oven dried for 12 hours to give 44.69 g of a mixture of 2-cyano-3-chloro-5-(methylthio)pyridine and 2-cyano-5-chloro-3-(methylthio)pyridine.

A solution of 3,4-dichlorophenol (44.69 g) in 200 ml of THF was added dropwise to a stirred solution of t-BuOK (31.78 g) in 150 ml of THF. A 43.60 g portion of the 2-cyano-3-chloro-5-(methylthio)pyridine/2-cyano-5-chloro-3-(methylthio)pyridine mixture noted above in 200 ml of THF was added and brought to reflux. DMSO (50 ml) was added and the resulting mixture refluxed for 28 hours. After reflux, the reaction mixture was cooled, poured onto ice and the yellow solid which formed was collected by filtration. The solid was dried and 65.73 g of a mixture of 2-cyano-3-(3,4-dichlorophenoxy)-5-(methylthio)pyridine and 2-cyano-5-(3,4-dichlorophenoxy)-3-(methylthio)pyridine obtained.

To a solution of $H_2SO_4$ (150 ml) and 50 ml $H_2O$ at 90° C. was added the mixture of 2-cyano-3-(3,4-dichlorophenoxy)-5-(methylthio)pyridine and 2-cyano-5-(3,4-dichlorophenoxy)-3-(methylthio)pyridine, (61.34 g). The resulting mixture was heated to 145° C. and stirred for 2 hours, cooled and poured onto 1 liter of ice. The precipitate was collected, washed with water and dried to give 65.03 g of a brown solid. A portion of the solid, (29.22 g), was washed with acetone to give 19.89 g of a light tan solid. The light tan solid was stirred with ethyl acetate and shaken with 1 N NaOH, which resulted in the formation of 2 layers. The basic layer was acidified with acetic acid, washed with water, then brine and dried ($Na_2SO_4$). Filtration and evaporation of the solvent, gave 15.0 g of a mixture of 3-(3,4-dichlorophenoxy)-5-(methylthio)-pyridine-2-carboxylic acid and 5-(3,4-dichlorophenoxy)-3-(methylthio)-pyridine-2-carboxylic acid.

To 1,2-dichlorobenzene (100 ml) at 150° C. was added 12.85 g of a mixture of 3-(3,4-dichlorophenoxy)-5-(methylthio)-pyridine-2-carboxylic acid and 5-(3,4-dichlorophenoxy)-3-(methylthio)-pyridine-2-carboxylic acid. The reaction mixture was stirred for an additional 15 minutes, then cooled and extracted with 6 N HCl (3×15 ml). The aqueous layers were combined, and upon standing, a solid formed. The solid was collected by filtration. The solid was stirred in $CH_2Cl_2$ and gradually dissolved upon addition of 25% NaOH. When the aqueous layer was strongly basic, the $CH_2Cl_2$ layer was separated, and the $CH_2Cl_2$ layer was washed with half-saturated brine, then brine, and dried ($Na_2SO_4$). The $CH_2Cl_2$ layer was then filtered and the solvent evaporated, which gave 9.82 g of a brown oil. The brown oil was distilled on a Kügelrohr distillation apparatus and 7.52 g of 3-(3,4-dichlorophenoxy)-5-(methylthio)pyridine was obtained as a yellow oil, which crystallized upon standing, m.p. 55° C.

The following compounds were prepared by oxidizing 3-(3,4-dichlorophenoxy)-5-(methylthio)pyridine employing oxidation procedures essentially as described herein.

EXAMPLE 76

3-(3,4-dichlorophenoxy)-5-(methylsulfinyl)pyridine, m.p. 66°-68° C.

The compound 3-(3,4-dichlorophenoxy)-5-(methylsulfinyl)pyridine was prepared by the oxidation of the corresponding methylthio compound with DABCO.2Br2 according to the procedure reported by Oae et al. (S. Oae, Y. Ohnishi, S. Kozuka and W. Tagaki, Bull. of Chem. Soc., Japan, 39, 364 (1966).

EXAMPLE 77

3-(3,4-dichlorophenoxy)-5-(methylsulfonyl)pyridine, m.p. 139°-140° C.

The physical properties of example numbers 27-77 are summarized in Table 2.

TABLE 2

| Compound Example Number | R —S(O)$_m$— R | m | R$_1$ | R$_2$ | R$_3$ | M.p. °C.*** B.p. (mmHg) | Calculated % C | % H | % N | Found % C | % H | % N |
|---|---|---|---|---|---|---|---|---|---|---|---|---|
| 27 | 5 CH$_3$ | 2 | 2 4-SCF$_3$ | H | H | 134-135 | 44.69 | 2.89 | 4.01 | 44.98 | 3.03 | 4.03 |
| 28 | 5 CH$_3$ | 2 | 2 4-O—⟨phenyl⟩ | H | H | 136.5-138 | 63.33 | 4.43 | 4.10 | 63.01 | 4.55 | 4.01 |
| 29 | 5 CH$_3$ | 2 | 2 4-Br | H | H | 125-126 | 43.91 | 3.07 | 4.27 | 43.65 | 3.29 | 4.34 |
| 30 | 5 CH$_3$ | 2 | 2 4-CN | H | H | 195-196 | 56.92 | 3.67 | 10.22 | 57.13 | 3.77 | 10.24 |

TABLE 2-continued $Y = $ cyclohexyl ring with substituents $R_1, R_2, R_3$; group $-S(O)_m-R$

| Compound Example Number | * R | m |  R₁ | R₂ | R₃ | M.p. °C.* B.p. (mmHg) | Calculated % C | % H | % N | Found % C | % H | % N |
|---|---|---|---|---|---|---|---|---|---|---|---|---|
| 31 | 5 CH₃ | 2 | 2 4-C(=O)-phenyl | H | H | 130–131.5 | 64.57 | 4.28 | 3.96 | 64.09 | 4.50 | 3.94 |
| 32 | 5 CH₃ | 2 | 2 4-Cl | H | H | 117–118 | 50.79 | 3.55 | 4.93 | 50.82 | 3.74 | 5.08 |
| 33 | 5 CH₃ | 2 | 2 4-t-butyl | H | H | 142 | 62.92 | 6.27 | 4.59 | 62.95 | 6.37 | 4.59 |
| 34 | 5 CH₃ | 2 | 2 4-C(=O)-CH₃ | H | H | 143–144 | 57.72 | 4.50 | 4.81 | 57.60 | 4.75 | 5.27 |
| 35 | 5 CH₃ | 2 | 2 3-Br | H | H | 134.5 | 43.91 | 3.07 | 4.27 | 43.58 | 3.29 | 4.29 |
| 36 | 5 CH₃ | 2 | 2 3-CN | H | H | 139 | 56.92 | 3.67 | 10.21 | 56.58 | 3.92 | 10.12 |
| 37 | 5 CH₃ | 2 | 2 4-SCH₃ | H | H | 128–130 | 52.86 | 4.44 | 4.74 | 52.63 | 4.46 | 4.66 |
| 38 | 5 CH₃ | 0 | 2 4-Cl | 3-Cl | H | 145/0.05 mm | 50.36 | 3.17 | 4.89 | 50.16 | 3.16 | 4.71 |
| 39 | 5 CH₃ | 1 | 2 4-Cl | 3-Cl | H | 88–90 | 47.69 | 3.00 | 4.64 | 47.67 | 3.09 | 4.65 |
| 40 | 5 CH₃ | 2 | 2 4-Cl | 3-Cl | H | 120–121 | 45.29 | 2.85 | 4.40 | 45.06 | 2.98 | 4.43 |
| 41 | 5 C₂H₅ | 2 | 2 3,4-methylenedioxy | H | H | 97–99 | 54.71 | 4.26 | 4.56 | 54.67 | 4.31 | 4.65 |
| 42 | 5 C₂H₅ | 2 | 2 4-Cl | H | H | 128–130 | 52.43 | 4.06 | 4.70 | 52.17 | 4.07 | 4.58 |
| 43 | 5 C₂H₅ | 2 | 2 4-C(=O)-phenyl | H | H | 131–132 | 65.37 | 4.66 | 3.81 | 64.91 | 4.66 | 3.65 |
| 44 | 5 C₂H₅ | 2 | 2 4-O-phenyl | H | H | 38–41 | 64.21 | 4.82 | 3.94 | 63.73 | 4.68 | 3.81 |
| 45 | 5 C₂H₅ | 0 | 2 4-Cl | 3-Cl | H | 145/0.05 mm | 52.01 | 3.69 | 4.67 | 52.32 | 3.60 | 4.53 |
| 46 | 5 C₂H₅ | 1 | 2 4-Cl | 3-Cl | H | 80–82 | 49.38 | 3.51 | 4.43 | 49.02 | 3.48 | 4.34 |
| 47 | 5 C₂H₅ | 2 | 2 4-Cl | 3-Cl | H | 117–118 | 47.00 | 3.34 | 4.22 | 46.78 | 3.43 | 4.13 |
| 48 | 5 C₂H₅ | 2 | 2 5-Cl | 4-Cl | 2-Cl | 120–122 | 42.58 | 2.75 | 3.82 | 42.71 | 2.83 | 3.80 |
| 49 | 5 (CH₃)₂CH | 2 | 2 4-Cl | 3-Cl | H | 91–92 | 48.56 | 3.78 | 4.05 | 48.92 | 3.82 | 3.95 |
| 50 | 5 (CH₃)₂CH | 2 | 2 4-Br | H | H | 93–94 | 47.20 | 3.96 | 3.93 | 47.16 | 4.11 | 3.96 |
| 51 | 5 (CH₃)₂CH | 2 | 2 4-C(=O)-phenyl | H | H | 113–114 | 66.12 | 5.02 | 3.67 | 65.86 | 5.12 | 3.68 |
| 52 | 5 (CH₃)₂CH | 2 | 2 4-C(=O)-CH₃ | H | H | 114–115 | 60.17 | 5.37 | 4.39 | 59.66 | 5.49 | 4.51 |
| 53 | 5 CH₃(CH₂)₅ | 2 | 2 4-Br | H | H | 94 | 51.26 | 5.06 | 3.52 | 50.92 | 5.13 | 3.62 |
| 54 | 5 CH₃(CH₂)₅ | 2 | 2 4-Cl | 3-Cl | H | 75.5 | 52.58 | 4.93 | 3.61 | 52.53 | 5.09 | 3.52 |
| 55 | 5 CH₃(CH₂)₅ | 2 | 2 4-C(=O)-phenyl | H | H | 72–74 | 68.06 | 5.95 | 3.31 | 67.24 | 6.19 | 3.30 |
| 56 | 5 cyclohexyl | 2 | 2 4-C(=O)-CH₃ | H | H | 116–118 | 63.48 | 5.89 | 3.90 | 62.72 | 6.10 | 3.99 |
| 57 | 5 cyclohexyl | 2 | 2 4-Br | H | H | 146.5–147 | 51.52 | 4.58 | 3.54 | 51.59 | 4.64 | 3.58 |
| 58 | 5 cyclohexyl | 2 | 2 4-Cl | 3-Cl | H | 114 | 52.85 | 4.44 | 3.63 | 52.74 | 4.60 | 3.78 |
| 59 | 5 cyclohexyl | 2 | 2 4-C(=O)-phenyl | H | H | 138–139 | 68.38 | 5.50 | 3.32 | 67.13 | 5.88 | 3.22 |
| 60 | 5 phenyl | 2 | 2 4-Cl | 3-Cl | H | 113–114 | 53.69 | 2.92 | 3.68 | 53.47 | 3.09 | 3.57 |
| 61 | 5 phenyl | 2 | 2 4-Br | H | H | 120–121 | 52.32 | 3.10 | 3.59 | 52.44 | 3.26 | 3.58 |
| 62 | 5 benzyl | 2 | 2 4-C(=O)-phenyl | H | H | 146–147 | 69.91 | 4.46 | 3.26 | 69.61 | 4.66 | 3.12 |
| 63 | 5 benzyl | 2 | 2 4-Cl | 3-Cl | H | 112–113 | 54.83 | 3.32 | 3.55 | 54.28 | 3.46 | 3.57 |

TABLE 2-continued $$Y = \text{phenyl ring with } R_1, R_2, R_3 \text{ substituents}$$

Structure: pyridine with $-S(O)_m R$ and $-OY$ substituents; $Y$ = phenyl ring with $R_1$, $R_2$, $R_3$.

| Compound Example Number | * | R | m | ** | $R_1$ | $R_2$ | $R_3$ | M.p. °C*** B.p. (mmHg) | Calculated % C | % H | % N | Found % C | % H | % N |
|---|---|---|---|---|---|---|---|---|---|---|---|---|---|---|
| 64 | 5 | benzyl | 2 | 2 | 4-Br | H | H | 130 | 53.47 | 3.49 | 3.47 | 53.27 | 3.63 | 3.37 |
| 65 | 4 | $CH_3$ | 2 | 2 | 4-Cl | 3-Cl | H | 95–96 | 45.29 | 2.85 | 4.40 | 45.59 | 2.99 | 4.25 |
| 66 | 2 | $CH_3$ | 2 | 4 | 4-Cl | 3-Cl | H | 91–93 | 45.29 | 2.85 | 4.40 | 44.96 | 2.86 | 4.30 |
| 67 | 6 | $CH_3$ | 2 | 2 | 4-Cl | 3-Cl | H | 90–91 | 45.29 | 2.85 | 4.40 | 45.07 | 2.74 | 4.33 |
| 68 | 6 | $CH_3$ | 2 | 2 | 4-C(O)-phenyl | H | H | 143–144 | 64.57 | 4.28 | 3.96 | 64.45 | 4.28 | 3.94 |
| 69 | 6 | $CH_3$ | 2 | 2 | 4-$CH_2$-phenyl | | | 200/0.1 | 67.23 | 5.05 | 4.13 | 67.19 | 5.22 | 4.11 |
| 70 | 6 | $CH_3$ | 2 | 2 | 4-Br | H | H | 81–82 | 43.91 | 3.07 | 4.27 | 43.89 | 3.12 | 4.33 |
| 71 | 3 | $CH_3$ | 2 | 2 | 4-Cl | 3-Cl | H | 95–96 | 45.29 | 2.85 | 4.40 | 45.16 | 2.80 | 4.22 |
| 72 | 3 | $CH_3$ | 2 | 2 | 4-C(O)-phenyl | H | H | 119–120 | 64.57 | 4.28 | 3.96 | 64.25 | 4.44 | 3.82 |
| 73 | 3 | $C_2H_5$ | 2 | 2 | 4-Cl | 3-Cl | H | 82 | 47.00 | 3.34 | 4.22 | 46.92 | 3.47 | 4.05 |
| 74 | 3 | $C_2H_5$ | 2 | 2 | 4-C(O)-phenyl | H | H | 149 | 65.37 | 4.66 | 3.81 | 65.35 | 4.70 | 3.76 |
| 75 | 5 | $CH_3$ | 0 | 3 | 4-Cl | 3-Cl | H | 55 | 50.36 | 3.17 | 4.89 | 50.49 | 3.25 | 4.82 |
| 76 | 5 | $CH_3$ | 1 | 3 | 4-Cl | 3-Cl | H | 66–68 | 47.69 | 3.00 | 4.64 | 47.83 | 3.07 | 4.61 |
| 77 | 5 | $CH_3$ | 2 | 3 | 4-Cl | 3-Cl | H | 139–140 | 45.29 | 2.85 | 4.40 | 45.25 | 2.89 | 4.26 |

*The position of the $-S(O)_m$ radical on the pyridine ring with regard to formula I.
**The position of the $-OY$ radical on the pyridine ring with regard to formula I.
***The values presented refer to either the melting point in degrees Centigrade or the boiling point in degrees Centigrade at a particular pressure indicated in millimeters of mercury.

The antiviral compounds of the invention have been found to be particularly effective against picornaviruses, i.e., the small ribonucleic acid viruses. The picornaviruses include viruses such as Coxsackieviruses, Rhinoviruses and a number of plant disease viruses. There is some compound-to-compound variation in antiviral potency and spectrum of antiviral activity, and in toxicity and side effects, as illustrated below.

It is believed that many of those compounds excluded from the scope of formula I (i.e., those isomers of the compounds described by formula I having m, R and Y definitions as for formula I but excluded by proviso) would also be expected to exhibit antiviral activity.

Antiviral activity for the subject compounds was demonstrated utilizing the following tissue culture testing procedure:

Monolayered HeLa cells in 16 millimeter (mm) tissue culture dishes were treated with 1 ml of culture medium (Eagles medium supplemented with fetal calf serum) containing subject compound at an appropriate concentration or containing no compound at all. Culture media such as those described herein are more fully described in standard texts, as for example, Kuchler's Biochemical Methods in Cell Culture and Virology, Dowden, Hutchinson and Ross, Inc., Stroudsberg, PA (1977). Following treatment, cells were challenged with 0.05 ml of rhinovirus type 1A (RV-1A), rhinovirus type 2 (RV-2) or Coxsackie $A_{21}$ virus (Cox $A_{21}$) in culture medium. Some of the compounds were also tested against rhinovirus type 5 (RV-5), rhinovirus type 8 (RV-8) or rhinovirus type 64 (RV-64). Cell controls received no viruses. Cultures were observed for compound cytotoxicity and viral cytopathic effect (CPE) at 48 and 72 hours post-treatment.

In addition, some of the compounds were tested in animals utilizing the following procedure, hereinafter referred to as the "Single Oral Dose" test. Swiss male mice, 8–12 grams in weight were challenged intraperitoneally (IP) with 0.2 ml of a normally lethal dose, i.e., a virus dose sufficient to cause ≈80–100% mortality in infected animals within 10 days of challenge of Cox $A_{21}$, in phosphate buffered saline containing 1% heat inactivated fetal calf serum. Three hours later mice were treated orally (P.O.) with 0.2 ml of compound suspended in 0.5% hydroxypropyl methylcellulose (Methocel) or with 0.2 ml of 0.5% Methocel containing no compound. Compound solutions had a concentration of 10 milligrams/milliliter (mg/ml), 20 mg/ml or 30 mg/ml, thus 0.2 ml of compound suspended in 0.5 percent Methocel represents a dosage of 200 milligrams/kilogram (mg/kg), 400 mg/kg or 600 mg/kg, respectively. Mice were observed daily for 7–10 days post-challenge and deaths recorded. A modified Mantel-Haenzel combined chi-square procedure was used to determine significant difference between virus control and treated groups. Chi-square values greater than 3.84 are considered significant (95% confidence level) in this test.

Some of the compounds were also tested in animals utilizing the following procedure, hereinafter referred to as the "Continuous Oral Feeding" test. Coxsackie $A_{21}$ virus grown on HeLa cells was administered at a concentration that produces 80 to 100% deaths in mice weighing 8 to 12 grams within 10 days, when the mice are injected (IP) with 0.2 ml of virus preparation. Mice were placed on diets containing test compound dispersed in plain commercially available rodent mash chow at a concentration of 0.06% (weight percent) on day 0. On day 1 the mice were challenged with the virus preparation, 0.2 ml/mouse, (IP). Deaths in both control and experimental groups were recorded for the 10 days and the results analyzed by a chi-square ($\chi^2$) test. Chi-square values greater than 3.84 indicate the compound is active (95% confidence level).

The results obtained from the testing described above are summarized in Table 3.

TABLE 3

| Example Number | Cytotoxicity[1] (μg/ml) | Tissue Culture Testing[2] (μg/ml) | | | | | | Single Oral Dose | | Continuous Oral Feeding | |
|---|---|---|---|---|---|---|---|---|---|---|---|
| | | RV-1A | RV-2 | Cox $A_{21}$ | RV-5 | RV-8 | RV-64 | Dose (mg/kg) | $\chi^2$ | Dose[3] | $\chi^2$ |
| 27 | ≧100 | 12.5 | <6.25 | <6.25 | NA | NA | <6.25 | 600 | 39.700 | 0.06% | 29.753 |
| 28 | >100 | NA | 25 | 50 | | | | | | 0.06% | 6.249 toxic |
| 29 | 50 | 0.625 | 0.625 | 5.0 | 25 | 6.25 | 0.625 | 600 | 5.275 | 0.06% | 20.885 |
| 30 | >100 | 50 | 50 | 6.25 | 50 | 25 | 25 | 600 | 30.960 | 0.06% | 24.144 |
| 31 | >100 | 12.5 | 5.0 | 0.125 | 6.25 | 6.25 | 2.5 | 600 | 19.383 | 0.06% | 24.397 |
| 32 | 50 | 1.25 | 2.5 | 3.125 | NA | NA | 1.25 | 200 | 52.866 | | |
| 33 | >100 | NA | 12.5 | NA | | | | | | 0.06% | 4.042 |
| 34 | >50 | 25 | 12.5 | NA | | | | | | 0.06% | 1.727 |
| 35 | >100 | <6.25 | 12.5 | 50 | NA | NA | 6.25 | 600 | 1.604 | 0.06% | 0.197 |
| 36 | >100 | 12.5 | 50 | 50 | NA | NA | 50 | 600 | 2.20 | 0.06% | 3.447 |
| 37 | >50 | <3 | <2 | 3 | | | | | | | |
| 38 | 25 | 1.25 | 2.5 | 2.5 | NA | NA | | 600 | 25.233 | | |
| 39 | 25 | 0.625 | 1.25 | 25 | NA | NA | 1.25 | | | | |
| 40 | 50 | ≦0.31 | 0.625 | ≦6.25 | 25 | ±12.5 | | 600 | 22.807 | | |
| 41 | ≧50 | NA | 25 | NA | | | NA | | | | |
| 42 | ≧50 | 6.25 | 3.125 | 3.125 | NA | ±50 | ≦3.125 | 600 | 46.453 | 0.06% | 17.64 |
| 43 | 25 | ≦3.125 | 6.25 | <<3.125 | 12.5 | 25 | 6.25 | 600 | 45.207 | 0.06% | 20.44 |
| 44 | 6.25 | 6.25 | 3.125 | 3.125 | NA | 6.25 | NA | 600 | 0.196 | 0.06% | 1.58 |
| 45 | 12.5 | 2.5 | 2.5 | 3.125 | NA | NA | 5 | | | | |
| 46 | 12.5 | <<3.125 | <<3.125 | 12.5 | NA | NA | 5 | | | | |
| 47 | >50 | 0.3125 | 0.625 | 2.5 | NA | NA | ≦0.3125 | 600 | 25.587 | 0.06% | 1.10 |
| 48 | >50 | <3.125 | 3.125 | 6.25 | | | | | | | |
| 49 | 12.5 | <0.3125 | 0.625 | 0.625 | NA | NA | 0.625 | 400 | 0.004 | 0.06% | 3.851 |
| 50 | 12.5 | 1.25 | 1.25 | 1.25 | NA | NA | 2.5 | 600 | 10.040 | 0.06% | 1.243 |
| 51 | 4.0 | 4.0 | 2.0 | NA | | | NA | 600 | 3.085 | 0.06% | 17.705 |
| 52 | ≧50 | 50 | 50 | 25 | | | | | | 0.06% | 1.140 |
| 53 | >50 | 25 | 25 | 12.5 | | | | | | 0.06% | 2.925 |
| 54 | >50 | 12.5 | 12.5 | NA | | | | | | 0.06% | 0.162 |
| 55 | 12.5 | 3.125 | 12.5 | 3.125 | | | | 600 | 0.190 | | |
| 56 | 12.5 | ±12.5 | ±12.5 | 3.125 | | | | | | 0.06% | 0.019 |
| 57 | 50 | 25 | 25 | 6.25 | | | | | | | |
| 58 | 50 | 25 | 12.5 | 25 | | | | | | | |
| 59 | 12.5 | 3.125 | 12.5 | <3.125 | | | | | | | |
| 60 | ≧100 | 5 | 10 | 10 | | | | 600 | 0.839 | 0.06% | 0.970 |
| 61 | 20 | 10 | 10 | 5 | | | | 600 | 4.401 | 0.06% | 3.328 |
| 62 | 50 (GI) | 25 | NA | <3.125 | | | | | | 0.06% | 0.066 |
| 63 | 25 | 5 | 10 | 10 | | | | 600 | 0.733 | 0.06% | 4.106 |
| 64 | ≧100 | NA | 50 | NA | | | | 600 | 0.483 | 0.06% | 2.985 |
| 65 | 50 | 25 | 25 | <3.125 | | | NA | | | | |
| 66 | 25 | 12.5 | 12.5 | 12.5 | | | NA | | | | |
| 67 | 50 | 3.125 | 12.5 | ±50 | | | | | | | |
| 68 | 12.5 | 6.25 | 6.25 | 6.25 | | | | | | 0.06% | 7.39 toxic |
| 69 | 5 | 0.625 | 2.5 | NA | NA | NA | NA | 600 | 0.362 | 0.06% | 0.680 |
| 70 | 25 | 25 | 25 | NA | | | | 600 | 3.510 | 0.06% | 0.776 |
| 71 | 50 | 25 | 50 | 50 | | | | | | 0.06% | 0.035 |
| 72 | 25 | 25 | 25 | 12.5 | | | | | | | |
| 73 | 25 | 25 | 25 | NA | | | | | | | |
| 74 | 50 | 50 | ±50 | NA | | | | | | | |
| 75 | 6.25 | 6.25 | 6.25 | 3.125 | | | | | | | |
| 76 | 25 | 12.5 | 6.25 | 25 | | | | | | | |
| 77 | >50 | 6.25 | 12.5 | 3.125 | | | | | | | |

[1]Cytotoxicity figures represent the concentration of the compound, micrograms/milliliter (μg/ml), found to be toxic to the cell.
[2]Lowest concentration of the compound (μg/ml) necessary to cause a 50 percent reduction in cytopathic effect.
[3]Percent (by weight) of test compound in the diet fed to test animals.
The symbol "NA" indicates that the compound was not active against that particular virus at the standard test conditions; "<" means "less than"; ">" means "greater than"; "≦" means "less than or equal to"; "≧" means "greater than or equal to"; "±" means "approximately"; "<<" means "considerably less than"; "GI" means "growth inhibition" and indicates that at the concentration shown the compound inhibited the growth of the tissue culture; and "toxic" means that the test compound was significantly toxic at the indicated dosage.

The data in Table 3 demonstrate the antiviral activity of representative compounds falling within the scope of the present invention.

The tissue culture test data indicate that the test compounds presented in Table 3 are active against at least one of the three test viruses, (RV-1A, RV-2 or Cox $A_{21}$). In addition, some of the test compounds have exhibited antiviral activity with respect to test viruses RV-5, RV-8 or RV-64. The compounds 2-(4-bromophenoxy)-6-(methylsulfonyl)pyridine, 2-(3,4-dichlorophenoxy)-3-(ethylsulfonyl)pyridine and (4-((3-ethylsulfonyl)-2-pyridinyl)oxy)phenyl)phenylmethanone were only marginally active but did exhibit activity against RV-1A and RV-2 at a test concentration equivalent to the cytotoxic concentration. The compound (4-((5-((1-methylethyl)sulfonyl)-2-pyridinyl)oxy)phenyl)phenyl-methanone did not show activity against the test viruses in its initial tissue culture testing but did show activity against RV-1A and RV-2 on retest (the retest data is presented in Table 3). The compound 1-(4-((6-(methylsulfonyl)-2-pyridinyl)oxy)phenyl)ethanone was prepared but was not active against RV-1A, RV-2 or Cox $A_{21}$ at the standard test conditions.

Some of the compounds have demonstrated (at the 95% confidence level, i.e., have a $\chi^2$ value greater than 3.84) that they are active antiviral compounds in testing with mice.

Of particular interest are those compounds which exhibit antiviral activity in both the "Single Oral Dose" and "Continuous Oral Feeding" tests. A compound which can be administered orally and still retain antiviral activity has distinct advantages since it can be readily incorporated into the diets of mammals, as exemplified in the "Continuous Oral Feeding" test, or administered to mammals orally in various compositions comprising the active compound and a pharmaceutically-acceptable carrier. Several of the test compounds have exhibited antiviral activity against a broad spectrum of viruses in other tissue culture testing as follows:

The test compound was dissolved in an appropriate solvent (generally dimethyl sulfoxide) and incubated at 56° C. for at least 15 minutes and this solution was then used to prepare various test solutions having the desired concentration of test compound in preheated WI maintenance medium (49% Eagles, 49% medium 199, 2% fetal calf serum and antibiotics).

Triplicate cell culture tubes (WI-38 human embryonic lung cell culture tubes) were fed with 1 ml of medium containing the compound at specified concentrations and inoculated with 3–300 TCID$_{50}$ (3–300 times the tissue culture infective dose 50, i.e., the dose required to infect 50% of the cell cultures tested). Simultaneous viral titrations were performed. The tissue cultures were supplemented with fresh medium when necessary (around 3–4 days) until viral titrations were completed.

The cell culture tubes were examined dialy for cytopathic effect. Tests were judged complete when virus control titration tubes showed 75% or greater destruction of cell sheets. Comparisons were made at that time with the percentage of cell sheet destruction in tubes containing virus compound mixtures. Observed differences of 75% or more were graded "+", 74–50% as "±", and less than 50% as "−" inhibition.

The results of the above described testing is shown in Table 4.

As indicated by the data in Table 4, several of the test compounds have inhibited the multiplication of most of the 20 different rhinoviruses against which they were tested.

At a concentration of 25 micrograms per milliliter (μg/ml), the compound (4-((5-(methylsulfonyl)-2-pyridinyl)oxy)phenyl)phenylmethanone was graded "+" against 13 different test rhinoviruses and "±" against 3 others; the compound 2-(3,4-dichlorophenoxy)-5-(methylsulfonyl)pyridine was graded "+" against 14 test rhinoviruses and "±" against 2 others; and the compound 2-(3,4-dichlorophenoxy)-5-(ethylsulfonyl)pyridine was graded "+" against 14 test viruses and "±" against 3 others.

At a concentration of 12.5 μg/ml, the compound 2-(4-chlorophenoxy)-5-(methylsulfonyl)pyridine was graded "+" against 13 test rhinoviruses and "±" against 3 others; and the compound 2-(4-chlorophenoxy)-5-(ethylsulfonyl)pyridine was graded "+" against 13 test rhinoviruses and "±" against 4 others.

Only the compound (4-((5-ethylsulfonyl)-2-pyridinyl)oxy)phenyl)phenylmethanone, which was tested at a 3.0 μg/ml concentration, failed to inhibit the multiplication of the majority of the 20 test rhinoviruses.

The results of the above-noted testing indicate that several of the test compounds are particularly effective against Picornaviruses, i.e., small ribonucleic acid (rna) viruses, as for example, the Coxsackieviruses and Rhinoviruses. The results further indicate that such compounds have a broad spectrum of activity against Picornaviruses.

Because of their distinct advantages, (for example, broad spectrum antiviral activity at low compound concentration) the compounds (4-((5-(methylsulfonyl)-2-pyridinyl)oxy)phenyl)phenylmethanone, 2-(3,4-dichlorophenoxy)-5-(methylsulfonyl)pyridine, 2-(3,4-dichlorophenoxy)-5-(ethylsulfonyl)pyridine, 2-(4-chlorophenoxy)-5-(methylsulfonyl)pyridine and 2-(4-chlorophenoxy)-5-(ethylsulfonyl)pyridine are the preferred embodiments of the present invention.

In using the subject compounds, a virus or virus host cell is contacted with an amount of one or more of the compounds effective to inhibit the virus. Although the invention should not be construed as limited to any particular theory of action, it appears that the compounds act to inhibit virus in host cells, rather than by direct chemical or physical inactivation of the virus particle apart from the cell. In antiviral applications carried out in non-living environments, contacting should be carried out in a manner which ensures continued presence of an effective amount of the compound when subsequent contact with host cells occurs. Preferably, the compounds are used by contacting the host cells with an effective antiviral amount (i.e., the amount which must be employed to achieve significant viral inhibition) of one or more of the compounds. The contacting can be carried out directly, as by addition of the

TABLE 4

| Compound Example Number | Test Concentration (μg/ml) | Hanks Untyped | Rhinovirus Type | | | | | | | | | | | | | | | | | |
|---|---|---|---|---|---|---|---|---|---|---|---|---|---|---|---|---|---|---|---|---|
| | | | 4 | 6 | 8 | 10 | 13 | 17 | 19 | 21 | 29 | 39 | 56 | 58 | 59 | 60 | 64 | 68 | 74 | 75 | 81 |
| 31 | 25 | + | + | ± | − | + | − | + | + | ± | + | − | + | + | + | + | ± | + | + | − | + |
| 32 | 12.5 | + | + | ± | − | + | − | + | + | ± | + | − | + | + | + | + | + | + | + | − | ± |
| 40 | 25 | + | − | − | − | + | + | + | + | + | + | + | + | + | ± | ± | + | + | + | − | + |
| 42 | 12.5 | + | + | + | − | ± | − | + | + | ± | + | − | ± | + | + | + | + | + | + | ± | + |
| 43 | 3.0 | ± | − | − | − | − | − | + | − | − | + | − | − | − | − | ± | − | ± | ± | − | + |
| 47 | 25 | + | + | ± | − | + | − | + | + | + | + | ± | + | + | ± | + | + | + | + | − | + | compound to cells in tissue culture, to inhibit contaminating picornaviruses. Contacting can also be carried out by administering an antiviral dosage of a compound of the invention to an animal (preferably, a mammal). The compounds can be administered to animals parenterally (for example, by intraperitoneal, subcutaneous or intravenous injection), topically (for example, used in an aerosol or skin lotion, or administered intranasally or buccally), rectally or orally, and the oral antiviral activity of certain of the compounds is a feature of the invention. In such applications, an effective antiviral dose of one or more of the compounds is administered to an animal. Selection of the compound or compounds for administration to animals in particular cases is dictated by considerations such as toxicity, mutagenicity, ease of administration, antiviral activity (potency), stability, compatibility with suitable carriers, etc.

The exact amount of the compound or compounds to be employed, i.e., the amount of the subject compound or compounds sufficient to provide the desired effect, depends on various factors such as the compound employed; type of contacting or administration; the size, age and species of animal; the route, time and frequency of administration; the virus or viruses involved, and whether or not the compound is administered prophylactically or is administered to an infected animal to inhibit the infecting virus. In particular cases, the amount to be administered can be ascertained by conventional range finding techniques, for example, by observing the effect produced at different rates using conventional virus assay procedures.

The compounds are preferably administered in the form of a composition comprising the compound in admixture with a pharmaceutically-acceptable carrier, i.e., a carrier which is chemically inert to the active compound and which has no detrimental side effects or toxicity under the conditions of use. As shown above, the compounds when administered to tissue culture medium exhibit significant antiviral activity at low concentrations, such as, for example, the 0.3125 μg/ml of 2-(3,4-dichlorophenoxy)-5-(ethylsulfonyl)pyridine which causes a 50% reduction in cytopathic effect in testing against test virus RV-1A.

Such compositions can contain from about 0.1 microgram or less of the active compound per milliliter of carrier to about 99 percent by weight of the active compound in combination with a pharmaceutically-acceptable carrier.

Preferred compositions include compositions containing from about 0.1 μg of active compound per milliliter of carrier to about 0.0025 to about 0.05 to about 0.25 to about 0.5 to about one to about 10 to about 25 to about 50 percent by weight of active compound in a pharmaceutically-acceptable carrier.

The compositions can be in solid forms such as tablets, capsules, granulations, feed mixes, feed supplements and concentrates, powders, granules, or the like; as well as liquid forms such as sterile injectable suspensions, orally administered suspensions, or solutions. The pharmaceutically-acceptable carriers can include excipients such as surface active dispersing agents, suspending agents, tableting binders, lubricants, flavors and colorants. Suitable excipients are disclosed, for example, in texts such as Remington's Pharmaceutical Manufacturing, Thirteenth Edition, Mack Publishing Co., Easton PA (1965).

What is claimed is:

1. An antiviral compound corresponding to the formula:

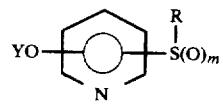

wherein m represents the integer 0, 1 or 2; R represents an alkyl group of from 1 to 7 carbon atoms, inclusive, a cycloalkyl group of 5 or 6 carbon atoms, or a Ar-$(CH_2)_q$- group wherein q represents the integer 0, 1, 2 or 3 and Ar represents an aryl group of from 6 to 10 carbon atoms, inclusive, which aryl group is optionally substituted with 1 to 3 substituents each independently selected from bromo, chloro, fluoro, methyl or methoxy; Y represents:

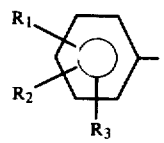

wherein $R_1$ and $R_2$ each independently represent hydrogen, bromo, chloro, fluoro, iodo, cyano, nitro, acetyl or the following moieties:

(a) a benzyl, phenoxy or benzoyl group, wherein the benzene ring of the benzyl, phenoxy or benzoyl group is optionally substituted with 1 to 3 substituents each independently selected from bromo, chloro, fluoro, methyl or methoxy;

(b) an alkyl group of 1 to 4 carbon atoms, inclusive, optionally substituted with 1 to 4 substituents each independently selected from bromo, chloro or fluoro;

(c) $R_4X$-, wherein X represents an oxygen or sulfur atom; and $R_4$ represents an alkyl group of from 1 to 3 carbon atoms, inclusive, the alkyl portion optionally substituted with 1 to 4 substituents each independently selected from bromo, chloro or fluoro; or (d) alternatively $R_1$ and $R_2$ taken together represent methylenedioxy; and $R_3$ represents hydrogen, bromo, chloro, fluoro or iodo; provided that:

(1) in those situations where the —OY radical is attached to the pyridine ring at the 3 position then the

radical is attached at the 5 position;

(2) in those situations where the —OY radical is attached to the pyridine ring at the 4 position then the

radical is attached at the 2 position;

(3) in those situations where m represents the integer 0 or 1; then:
  (i) the radical —OY must be attached to the pyridine ring at the 2 position and the:

radical at either the 3 or 5 positions; or (ii) the radical —OY must be attached to the pyridine ring at the 3 position and the:

radical at the 5 position; and (4) in those situations where R is Ar-(CH$_2$)$_q$- or optionally substituted Ar-(CH$_2$)$_q$- and R$_2$ and R$_3$ are both hydrogen, then R$_1$ is a substituent other than hydrogen.

2. The compound of claim 1 wherein m represents the integer 0, 1 or 2; R represents methyl or ethyl; R$_1$ represents benzoyl, bromo or chloro; and R$_2$ and R$_3$ each independently represent hydrogen, bromo or chloro.

3. The compound of claim 2 wherein m represents the integer 2; R represents methyl or ethyl; R$_1$ represents bromo or chloro; R$_2$ represents hydrogen, bromo or chloro; and R$_3$ represents hydrogen.

4. An antiviral compound corresponding to the formula:

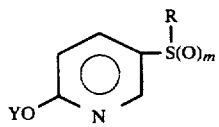

wherein m represents the integer 0, 1 or 2; R represents an alkyl group of from 1 to 7 carbon atoms, inclusive, cyclohexyl, phenyl, or benzyl; Y represents

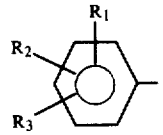

wherein R$_1$ and R$_2$ each independently represent hydrogen, bromo, chloro, fluoro, iodo, cyano, nitro, acetyl, or the following moieties:

(a) a benzyl, phenoxy or benzoyl group, wherein the benzene ring of the benzyl, phenoxy or benzoyl group is optionally substituted with 1 to 3 substituents each independently selected from bromo, chloro, fluoro, methyl or methoxy;

(b) an alkyl group of 1 to 4 carbon atoms, inclusive, optionally substituted with 1 to 4 substituents each independently selected from bromo, chloro or fluoro;

(c) R$_4$X-, wherein X represents an oxygen or sulfur atom; and R$_4$ represents an alkyl group of from 1 to 3 carbon atoms, inclusive, the alkyl portion optionally substituted with 1 to 4 substituents each independently selected from bromo, chloro or fluoro; or (d) alternatively R$_1$ and R$_2$ taken together represent methylenedioxy; and R$_3$ represents hydrogen, bromo, chloro, fluoro or iodo; provided that when R is benzyl or phenyl and R$_2$ and R$_3$ are both hydrogen, R$_1$ is a substituent other than hydrogen.

5. The compound of claim 4 wherein R represents an alkyl group of from 1 to 7 carbon atoms, inclusive, and R$_1$ and R$_2$ each independently represent hydrogen, bromo, chloro, fluoro, benzoyl, trifluoromethylthio, methylthio or cyano; and R$_3$ represents hydrogen, bromo, chloro or fluoro.

6. The compound of claim 5 wherein R represents methyl or ethyl.

7. The compound of claim 6 wherein R$_1$ represents benzoyl, bromo or chloro; and R$_2$ and R$_3$ each independently represent hydrogen, bromo or chloro.

8. The compound of claim 7 wherein R$_1$ represents bromo or chloro.

9. The compound of claim 8 wherein m represents the integer 1 or 2.

10. The compound of claim 9 wherein R$_1$ represents bromo or chloro; R$_2$ represents hydrogen, bromo or chloro; and R$_3$ represents hydrogen.

11. The compound of claim 10 wherein m represents the integer 2.

12. A compound selected from the group consisting of PO 5-(methylsulfonyl)-2-(4-((trifluoromethyl)thio)-phenoxy)pyridine,
5-(methylsulfonyl)-2-(4-phenoxyphenoxy)pyridine,
2-(4-bromophenoxy)-5-(methylsulfonyl)pyridine,
4-((5-(methylsulfonyl)-2-pyridinyl)oxy)benzonitrile,
(4-((5-(methylsulfonyl)-2-pyridinyl)oxy)phenyl)phenylmethanone,
2-(4-chlorophenoxy)-5-(methylsulfonyl)pyridine,
2-(4-(1,1-dimethylethyl)phenoxy)-5-(methylsulfonyl)-pyridine,
1-(4-((5-(methylsulfonyl)-2-pyridinyl)oxy)phenyl)ethanone,
2-(3-bromophenoxy)-5-(methylsulfonyl)pyridine,
3-((5-(methylsulfonyl)-2-pyridinyl)oxy)benzonitrile,
2-(4-(methylthio)phenoxy)-5-(methylsulfonyl)pyridine,
2-(3,4-dichlorophenoxy)-5-(methylthio)pyridine,
2-(B 3,4-dichlorophenoxy)-5-(methylsulfinyl)pyridine,
2-(3,4-dichlorophenoxy)-5-(methylsulfonyl)pyridine,
5-(ethylsulfonyl)-2-(3,4-methylenedioxyphenoxy)pyridine,
2-(4-chlorophenoxy)-5-(ethylsulfonyl)pyridine,
(4-((5-(ethylsulfonyl)-2-pyridinyl)oxy)phenyl)phenylmethanone,
5-(ethylsulfonyl)-2-(4-phenoxyphenoxy)pyridine,
2-(3,4-dichlorophenoxy)-5-(ethylthio)pyridine,
2-(3,4-dichlorophenoxy)-5-(ethylsulfinyl)pyridine,
2-(3,4-dichlorophenoxy)-5-(ethylsulfonyl)pyridine,
5-(ethylsulfonyl)-2-(2,4,5-trichlorophenoxy)pyridine,
2-(3,4-dichlorophenoxy)-5-((1-methylethyl)sulfonyl)-pyridine,
2-(4-bromophenoxy)-5-((1-(methylethyl)sulfonyl)pyridine,
(4-((5-((1-methylethyl)sulfonyl-2-pyridinyl)oxy) phenyl)phenylmethanone,
1-(4-((5-((1-methylethyl)sulfonyl-2-pyridinyl)oxy)-phenyl)ethanone,
2-(4-bromophenoxy)-5-(n-hexylsulfonyl)pyridine,
2-(3,4-dichlorophenoxy)-5-(n-hexylsulfonyl)pyridine,
(4-((5-n-hexylsulfonyl)-2-pyridinyl)oxy)phenyl)phenylmethanone,
1-(4-((5-(cyclohexylsulfonyl)-2-pyridinyl)oxy)phenyl)ethanone,
2-(4-bromophenoxy)-5-(cyclohexylsulfonyl)pyridine,
2-(3,4-dichlorophenoxy)-5-(cyclohexylsulfonyl)pyridine,
(4-((5-cyclohexylsulfonyl)-2-pyridinyl)oxy)phenyl)-phenylmethanone, 2-(3,4-dichlorophenoxy)-5-(phenylsulfonyl)pyridine,
2-(4-bromophenoxy)-5-(phenylsulfonyl)pyridine,
phenyl(4-((5-((phenylmethyl)sulfonyl)-2-pyridinyl)oxy)phenyl)methanone,
2-(3,4-dichlorophenoxy)-5-((phenylmethyl)sulfonyl)pyridine,
2-(4-bromophenoxy)-5-((phenylmethyl)sulfonyl)pyridine,
2-(3,4-dichlorophenoxy)-4-(methylsulfonyl)pyridine,
4-(3,4-dichlorophenoxy)-2-(methylsulfonyl)pyridine,
2-(3,4-dichlorophenoxy)-6-(methylsulfonyl)pyridine,
(4-((6-(methylsulfonyl)-2-pyridinyl)oxy)phenyl)phenylmethanone,
2-(methylsulfonyl)-6-(4-(phenylmethyl)phenoxy)pyridine,
2-(4-bromophenoxy)-6-(methylsulfonyl)pyridine,
2-(3,4-dichlorophenoxy)-3-(methylsulfonyl)pyridine,
(4-((3-(methylsulfonyl)-2-pyridinyl)oxy)phenyl)phenylmethanone,
2-(3,4-dichlorophenoxy)-3-(ethylsulfonyl)pyridine,
(4-((3-(ethylsulfonyl)-2-pyridinyl)oxy)phenyl)phenylmethanone,
3-(3,4-dichlorophenoxy)-5-(methylthio)pyridine,
3-(3,4-dichlorophenoxy)-5-(methylsulfinyl)pyridine, and
3-(3,4-dichlorophenoxy)-5-(methylsulfonyl)pyridine.

13. The compound of claim 12 which is 5-(methylsulfonyl)-2-(4-((trifluoromethyl)thio)phenoxy)pyridine.

14. The compound of claim 12 which is 5-(methylsulfonyl)-2-(4-phenoxyphenoxy)pyridine.

15. The compound of claim 12 which is 2-(4-bromophenoxy)-5-(methylsulfonyl)pyridine.

16. The compound of claim 12 which is 4-((5-(methylsulfonyl)-2-pyridinyl)oxy)benzonitrile.

17. The compound of claim 12 which is (4-((5-(methylsulfonyl)-2-pyridinyl)oxy)phenyl)phenylmethanone.

18. The compound of claim 12 which is 2-(4-chlorophenoxy)-5-(methylsulfonyl)pyridine.

19. The compound of claim 12 which is 2-(3,4-dichlorophenoxy)-5-(methylthio)pyridine.

20. The compound of claim 12 which is 2-(3,4-dichlorophenoxy)-5-(methylsulfinyl)pyridine.

21. The compound of claim 12 which is 2-(3,4-dichlorophenoxy)-5-(methylsulfonyl)pyridine.

22. The compound of claim 12 which is 5-(ethylsulfonyl)-2-(3,4-methylenedioxyphenoxy)pyridine.

23. The compound of claim 12 which is 2-(4-chlorophenoxy)-5-(ethylsulfonyl)pyridine.

24. The compound of claim 12 which is (4-((5-(ethylsulfonyl)-2-pyridinyl)oxy)phenyl)phenylmethanone.

25. The compound of claim 12 which is 2-(3,4-dichlorophenoxy)-5-(ethylthio)pyridine.

26. The compound of claim 12 which is 2-(3,4-dichlorophenoxy)-5-(ethylsulfinyl)pyridine.

27. The compound of claim 12 which is 2-(3,4-dichlorophenoxy)-5-(ethylsulfonyl)pyridine.

28. The compound of claim 12 which is 2-(3,4-dichlorophenoxy)-4-(methylsulfonyl)pyridine.

29. The compound of claim 12 which is 4-(3,4-dichlorophenoxy)-2-(methylsulfonyl)pyridine.

30. The compound of claim 12 which is 2-(3,4-dichlorophenoxy)-6-(methylsulfonyl)pyridine.

31. The compound of claim 12 which is 2-(4-(methylthio)phenoxy)-5-(methylsulfonyl)pyridine.

32. The compound of claim 12 which is 3-(3,4-dichlorophenoxy)-5-(methylsulfinyl)pyridine.

33. The compound of claim 12 which is 2-(3,4-dichlorophenoxy)-5-((phenylmethyl)sulfonyl)pyridine.

34. The compound of claim 12 which is 3-(3,4-dichlorophenoxy)-5-(methylsulfonyl)pyridine.

35. A method for inhibiting viruses which comprises contacting viruses or virus host cells with an effective virus inhibiting amount of a compound according to claim 1.

36. The method of claim 35 wherein the compound is contacted with a virus host cell.

37. The method of claim 35 wherein the compound is contacted with virus and mammalian cells.

38. The method of claim 35 wherein the viruses are picornaviruses.

39. The method of claim 35 wherein m represents the integer 0, 1 or 2; R represents methyl or ethyl; $R_1$ represents benzoyl, bromo or chloro; $R_2$ and $R_3$ each independently represent hydrogen, bromo or chloro.

40. The method of claim 39 wherein $R_1$ represents bromo or chloro; $R_2$ represents hydrogen, bromo or chloro; and $R_3$ represents hydrogen.

41. The method of claim 39 wherein the compound is (4-((5-(methylsulfonyl)-2-pyridinyl)oxy)phenyl)phenylmethanone.

42. The method of claim 39 wherein the compound is 2-(4-chlorophenoxy)-5-(methylsulfonyl)pyridine.

43. The method of claim 39 wherein the compound is 2-(3,4-dichlorophenoxy)-5-(methylsulfonyl)pyridine.

44. The method of claim 39 wherein the compound is 2-(4-chlorophenoxy)-5-(ethylsulfonyl)pyridine.

45. The method of claim 39 wherein the compound is 2-(3,4-dichlorophenoxy)-5-(ethylsulfonyl)pyridine.

46. A method useful for inhibiting viruses which comprises administering to an animal an effective virus inhibiting amount of a compound according to claim 1.

47. The method of claim 46 wherein the animal is a mammal.

48. The method of claim 46 wherein the animal is an animal infected with picornavirus.

49. The method of claim 48 wherein the picornavirus is a Rhinovirus.

50. The method of claim 48 wherein the picornavirus is a Coxsackievirus.

51. The method of claim 46 wherein m represents the integer 0, 1 or 2; R represents methyl or ethyl; $R_1$ represents benzoyl, bromo or chloro; $R_2$ and $R_3$ each independently represent hydrogen, bromo or chloro.

52. The method of claim 51 wherein $R_1$ represents bromo or chloro; $R_2$ represents hydrogen, bromo or chloro; and $R_3$ represents hydrogen.

53. The method of claim 51 wherein the compound is (4-((5-(methylsulfonyl)-2-pyridinyl)oxy)phenyl)phenylmethanone.

54. The method of claim 51 wherein the compound is 2-(4-chlorophenoxy)-5-(methylsulfonyl)pyridine.

55. The method of claim 51 wherein the compound is 2-(3,4-dichlorophenoxy)-5-(methylsulfonyl)pyridine.

56. The method of claim 51 wherein the compound is 2-(4-chlorophenoxy)-5-(ethylsulfonyl)pyridine.

57. The method of claim 51 wherein the compound is 2-(3,4-dichlorophenoxy)-5-(ethylsulfonyl)pyridine.

58. A composition for inhibiting viruses comprising an inert carrier in combination with an effective virus inhibiting amount of a compound according to claim 1.

59. The composition of claim 58 wherein the inert carrier is a non-toxic carrier.

60. The composition of claim 59 wherein the non-toxic carrier is a pharmaceutically-acceptable carrier.

61. The composition of claim 58 wherein m represents the integer 0, 1 or 2; R represents methyl or ethyl; $R_1$ represents benzoyl, bromo or chloro; $R_2$ and $R_3$ each independently represent hydrogen, bromo or chloro.

62. The composition of claim 61 wherein $R_1$ represents bromo or chloro; $R_2$ represents hydrogen, bromo or chloro; and $R_3$ represents hydrogen.

63. The composition of claim 61 wherein the compound is (4-((5-(methylsulfonyl)-2-pyridinyl)oxy)phenyl)phenylmethanone.

64. The composition of claim 61 wherein the compound is 2-(4-chlorophenoxy)-5-(methylsulfonyl)pyridine.

65. The composition of claim 61 wherein the compound is 2-(3,4-dichlorophenoxy)-5-(methylsulfonyl)pyridine.

66. The composition of claim 61 wherein the compound is 2-(4-chlorophenoxy)-5-(ethylsulfonyl)pyridine.

67. The composition of claim 61 wherein the compound is 2-(3,4-dichlorophenoxy)-5-(ethylsulfonyl)pyridine.

* * * * *